United States Patent
Xiang et al.

(10) Patent No.: US 10,640,476 B2
(45) Date of Patent: May 5, 2020

(54) BICYCLIC HETEROARYL DERIVATIVES AND PREPARATION AND USES THEREOF

(71) Applicant: XW LABORATORIES INC., Grand Cayman (KY)

(72) Inventors: Jia-Ning Xiang, Wuhan (CN); Xuesong Xu, Wuhan (CN); Wei Zhou, Wuhan (CN)

(73) Assignee: XW LABORATORIES INC., Grand Cayman (KY)

( * ) Notice: Subject to any disclaimer, the term of this patent is extended or adjusted under 35 U.S.C. 154(b) by 0 days.

(21) Appl. No.: 16/587,571

(22) Filed: Sep. 30, 2019

(65) Prior Publication Data

US 2020/0017456 A1    Jan. 16, 2020

Related U.S. Application Data

(63) Continuation of application No. PCT/CN2017/078873, filed on Mar. 30, 2017.

(51) Int. Cl.
| | |
|---|---|
| C07D 277/82 | (2006.01) |
| C07D 293/12 | (2006.01) |
| A61K 31/41 | (2006.01) |
| A61P 23/00 | (2006.01) |
| A61K 9/00 | (2006.01) |
| A61K 9/70 | (2006.01) |
| A61K 31/428 | (2006.01) |

(52) U.S. Cl.
CPC .......... *C07D 293/12* (2013.01); *A61K 9/0053* (2013.01); *A61K 9/7023* (2013.01); *A61K 31/41* (2013.01); *A61K 31/428* (2013.01); *A61P 23/00* (2018.01); *C07D 277/82* (2013.01)

(58) Field of Classification Search
CPC ............................ C07D 277/82; C07D 293/12
See application file for complete search history.

(56) References Cited

U.S. PATENT DOCUMENTS

| | | | | |
|---|---|---|---|---|
| 4,370,338 A | * | 1/1983 | Mizoule | C07D 277/82 514/367 |
| 6,489,350 B1 | * | 12/2002 | Benedyk | A61K 31/423 514/375 |
| 7,482,429 B2 | | 1/2009 | Albericio et al. | |
| 9,309,182 B2 | | 4/2016 | Tung et al. | |
| 2005/0182045 A1 | | 8/2005 | Nagase et al. | |
| 2010/0144869 A1 | | 6/2010 | Nudelman et al. | |
| 2012/0283300 A1 | | 11/2012 | Kim et al. | |
| 2016/0052862 A1 | | 2/2016 | Frost et al. | |

FOREIGN PATENT DOCUMENTS

| | | | | |
|---|---|---|---|---|
| CN | | 1422278 | 6/2003 | |
| CN | | 101511388 | 9/2006 | |
| CN | | 102076342 | 5/2011 | |
| CN | | 102834098 | 12/2012 | |
| CN | | 103370289 | 10/2013 | |
| DE | | 852392 | 10/1952 | |
| FR | | 2662695 | 2/2004 | |
| JP | | 2004059452 | 2/2004 | |
| WO | | 99/41275 | 8/1999 | |
| WO | | 99/51613 | 10/1999 | |
| WO | | 2005/123731 | 12/2005 | |
| WO | | 2009/102462 | 8/2009 | |
| WO | | 2009/137717 | 11/2009 | |
| WO | | 2010/124046 | 10/2010 | |
| WO | | 2013/019561 | 2/2013 | |
| WO | | 2014/031840 | 2/2014 | |
| WO | | 2014/152263 | 9/2014 | |
| WO | | 2014/205393 | 12/2014 | |
| WO | WO-2015/057884 A1 | * | 4/2015 | ........... A61K 31/428 |
| WO | | 2015/083129 | 6/2015 | |
| WO | | 2018/098472 | 5/2018 | |

OTHER PUBLICATIONS

Chemical Abstracts Registry No. 1744-22-5, indexed in the Registry file Nov. 16, 1984. (Year: 1984).*
Chemical Abstracts Registry No. 1243631-58-4, indexed in the Registry file Sep. 29, 2010. (Year: 2010).*
Chemical Abstracts Registry No. 60388-38-7, indexed in the Registry file Nov. 16, 1984. (Year: 1984).*
Chemical Abstracts Registry No. 60176-62-7, indexed in the Registry file Nov. 16, 1984. (Year: 1984).*
Chemical Abstracts Registry No. 326-45-4, indexed in the Registry file Nov. 16, 1984. (Year: 1984).*
Chemical Abstracts Registry No. 142229-71-8 {indexed in the Registry file Jul. 3, 1992. (Year: 1992).*
International Search Report and Written Opinion for International Application No. PCT/CN2018/090151, dated Feb. 20, 2019, 14 pages.
International Search Report and Written Opinion for International Application No. PCT/CN2018/097241, dated Apr. 28, 2019, 11 pages.
International Search Report and Written Opinion for International Application No. PCT/CN2018/118565, dated Jul. 8, 2019, Apr. 28, 2019, 13 pages.

(Continued)

*Primary Examiner* — Laura L Stockton

(57) ABSTRACT

The present invention relates compounds of Formula (A), as well as their preparation and uses, and further relates pharmaceutical compositions comprising these compounds and their uses as modulators of dysfunctional glutamate transmission. The present invention also relates to uses of the compounds or pharmaceutical compositions in treating or preventing certain neurological and psychiatric disorders and diseases as well as cancer in humans.

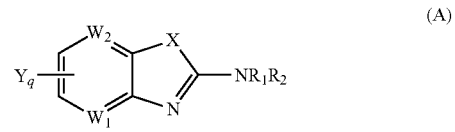

(A)

16 Claims, 3 Drawing Sheets

(56) References Cited

OTHER PUBLICATIONS

Ward et al., "Discovery of an Orally Bioavailable Nki Receptor Antagonist, (2S, 3S)-(2-Methoxy-5-tetrazol-I-ylbenzyl)(2-phenylpiperidin-3-yl)amine (GR203040), with Potent Antiemetic Activity," Journal of Med. Chem., 1995, vol. 38, p. 4985-4992.

International Search Report and Written Opinion for International Application No. PCT/CN2016/099763, dated Jan. 3, 2017, 15 pages.

International Search Report and Written Opinion for International Application No. PCT/CN2017/078873, dated Jan. 9, 2018, 12 pages.

International Search Report and Written Opinion for International Application No. PCT/CN2018/109115, dated Jul. 8, 2019, 11 pages.

Ahn et al., "Hapten and Antibody Production for a Sensitive immunoassay Determining a Human Urinary Metabolite of the Pyrethroid Insecticide Permethrin," J. Agriculture Food Chemistry, Jun. 2004, vol. 52, No. 15, p. 4583-4594.

Kaname et al., "One-pot copper-catalyzed tandem addition-cyclization of 2-iodoanilines with isoselenocyanates for the practical preparation of 2-aminobenzoselenazoles," Tetrahedron Letters, Nov. 2010, vol. 52, p. 505-508.

Lee et al., "Development of an Immunoassay for the Residues of the Herbicide Bensulfuron-Methyl," Journal Agriculture Food Chemistry, vol. 50, No. 7, p. 1791-1803, Feb. 2002.

Staldweiser et al., "Combinatorial Solid-Phase Synthesis of Structurally Complex Thiazolylhydantoines," Agnew Chem Int. Ed., Dec. 1998, Col. 37, No. 10, p. 1402-1404.

STN Columbus, Registry Jul. 21, 1990, 81055-72-3, 128321-03-9.
STN Columbus, Registry Dec. 4, 2015, CAS No. 1822708-15-5.
RN 1211588-05-4, STN REG, Mar. 19, 2010.
RN 1354448-66-0, STN REG, Jan. 25, 2012.
RN 1206250-52-3, STN REG, Feb. 12, 2010.
RN 1206250-51-2, STN REG, Feb. 12, 2010.
RN 1206250-54-5, STN REG, Feb. 12, 2010.
RN 1206248-58-9, STN REG, Feb. 12, 2010.
RN 747353-64-6 STN REG, Sep. 17, 2004.
RN 60176-63-8, STN REG, Nov. 16, 1984.

Rynearson et al., "2-Aminobenzoxazole ligands of the hepatitis C virus internal ribosome entry site," Bioorganic & Medicinal Chemistry Letters, Jun. 2014, vol. 24, p. 3521-3525.

\* cited by examiner

BICYCLIC HETEROARYL DERIVATIVES AND PREPARATION AND USES THEREOF

This application claims the benefit under 35 U.S.C. § 111(a) of PCT International Application No. PCT/CN2017/078873 filed on Mar. 30, 2017, which is incorporated by reference in its entirety.

FIELD

The present invention relates to the field of medicinal technology, in particular, to certain compounds, their preparation and uses, as well as pharmaceutical compositions comprising such compounds. As exemplified, the present invention relates to certain bicyclic heteroaryl derivatives, their preparation, and the corresponding pharmaceutical compositions. The compounds and/or pharmaceutical compositions of the present invention can be potentially used in the manufacture of a medicament for preventing, treating, ameliorating certain disorder or a disease in a patient, which includes, inter alia, a neurological or psychiatric disorder or disease, as well as a cancer. It is believed that the compounds and/or pharmaceutical compositions of the present invention exert their therapeutic benefits by, among other things, acting to modulate (e.g., block) dysfunctional glutamate transmission.

BACKGROUND

Based on clinical findings and evidence from their relevant preclinical models, dysfunctional glutamate transmission has important roles in a variety of disease pathologies. In the progression of these diseases, the underlying mechanisms for glutamate's release and/or uptake significantly involve its intercellular transmission caused by abnormal intercellular ion flows through respective cellular membrane's ion channels. As indicated below, the modulation (e.g., blockade) of these channels by published drugs (either directly, or via inducing a cascade of intervening pathways) can attenuate such disease progression.

Many neurological and psychiatric diseases involve dysfunctional glutamate transmission caused by abnormal Na and/or Ca activated K (also known as KCa2, SK) ion channels—(e.g., A. Doble, The Role of Excitotoxicity in Neurodegenerative Disease: Implications for Therapy, *Pharmacol. Ther.* Vol. 81 (3), pp. 163-221 and J. Lam, et. al. The Therapeutic Potential of Small-Conductance KCa2 Channels in Neurodegenerative and Psychiatric Diseases, *Expert Opin Ther Targets* Vol. 17(10), pp. 1203-1220). Such neurodegenerative diseases include amyotrophic lateral sclerosis (ALS), chronic pain such as neuropathy, multiple sclerosis (MS), ataxia, Parkinson's disease, Huntington's disease, Tourette syndrome, epilepsy, dystonia, Fragile X syndrome and disorders resulting from traumatic brain/spinal cord injuries or from cerebral ischemia. Psychiatric diseases include depression, anxiety, bipolar disorder, schizophrenia, obsessive compulsive disorder, autism, glaucoma induced optical neuropathy and alcohol/drug addiction. Cognitive dysfunctions include but not limited to dementia (vascular and Alzheimer's disease) and attention deficit/hyperactive disorder (ADHD). Unfortunately when the above mentioned diseases/disorders are progressive, they resist currently approved drug therapies at late stages or become resistant after starting drug therapies at earlier stages. For example in major depression, significant patient populations (10-55% depending on the database accessed) are/become 'treatment resistant'. In epilepsy, a significant minority (20-30%) of patients are/become resistant to currently approved drugs. Epilepsy, a complex neurological disorder estimated to affect over 50 million people worldwide, is characterized by recurrent spontaneous seizures due to neuronal hyperexcitability and hypersynchronous neural firing. Despite the availability of more than 20 antiepileptic drugs (AEDs), 30% of patients with epilepsy continue to experience seizures or suffer from undesirable drug side effects such as drowsiness, behavior changes, liver damage or teratogenicity.

In addition, the glutamate uptake involving tumor cell's Na-receptor channels is believed to potentiate cancer metastasis (e.g., M. B. A. Djamgoz, Persistent Current Blockers of Voltage-Gated Sodium Channels: A Clinical Opportunity for Controlling Metastatic Disease, *Recent Pat Anticancer Drug Discov.* Vol. 8(1), pp. 66-84 and T. Koltai, Voltage-gated sodium channel as a target for metastatic risk reduction with re-purposed drugs, *F1000 Research* Vol. 4, p. 297). In a Phase 2 clinical trial of patients having metastatic melanoma and then treated with Riluzole (for which the current marketing approval is only to treat ALS. In the clinical trial, metastasis was initially stabilized in 42% despite no overall improvement of RECIST grade. To further improve Riluzole's efficacy to treat metastatic melanoma, a combination therapy with other anticancer drugs was proposed.

Therefore, novel drugs are urgently needed to treat these 'resistant' patients whether as monotherapy or integrated into combination regimens (e.g., some combinations of existing drugs to treat epilepsy: N. Matsumura, Isobolographic analysis of the mechanisms of action of anticonvulsants from a combination effect, *European Journal of Pharmacology*, Vol. 741, pp. 237-246).

The compounds and pharmaceutical formulations disclosed in the present application are believed to be effective in providing the needed solution of achieving modulation of dysfunctional glutamate transmission for the aforementioned therapeutic indications.

SUMMARY

The following is only an overview of some aspects of the present invention, but is not limited thereto. All references of this specification are incorporated herein by reference in their entirety. When the disclosure of this specification is different with citations, the disclosure of this specification shall prevail. The present invention provides compounds and pharmaceutical compositions which modulates dysfunctional glutamate transmission via sodium channels and KCa2 channels, which include certain bicyclic heteroaryl derivatives, their preparation, and the corresponding pharmaceutical compositions. The compounds and/or pharmaceutical compositions of the present invention can be potentially used in the manufacture of a medicament for preventing, treating, ameliorating certain disorder or a disease in a patient, which includes, inter alia, a neurological or psychiatric disorder or disease, as well as a cancer.

One aspect of the present invention is the provision of a compound of Formula (A):

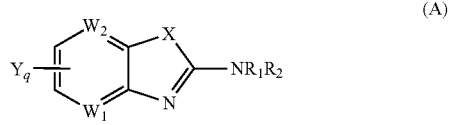

wherein,
X is NH, O, S or Se;
W$_1$ or W$_2$ is CH or N, provided that W$_1$ and W$_2$ are not both N;
R$_1$ and R$_2$ are the same, or they are different, and are independently selected from the group consisting of: hydrogen and
GR$^a$, wherein G is absent, —C(O)— or —C(O)O— and R$^a$ is a saturated straight or branched alkyl of from one to four carbon atoms, or a saturated cycloalkyl of from three to six carbon atoms, provided that R$_1$ and R$_2$ are not both GR$^a$, wherein G is not absent;
Y$_q$ is selected from the group consisting of hydrogen, deuterium, SF$_5$, CF$_3$, OCF$_3$, SCF$_3$, S(O)CF$_3$, S(O)$_2$CF$_3$, CN, SCN, S(O)CH$_3$, S(O)$_2$CH$_3$, NO$_2$, and wherein q is 1 or 2; provided that when q is 2, Y$_1$ and Y$_2$ can be the same, or different, and they are not both hydrogen, or both deuterium, or one each of hydrogen and deuterium;
or a pharmaceutically acceptable salt thereof, and with the proviso that when W$_1$ and W$_2$ are CH, the compound of Formula (A) is not one of the following compounds:

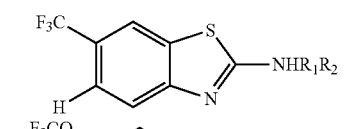
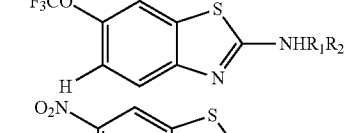
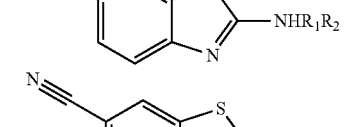
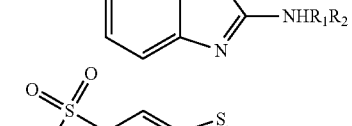
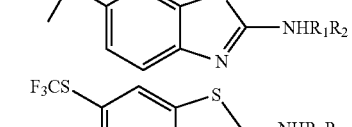
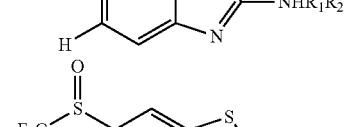
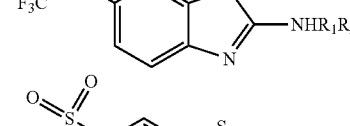
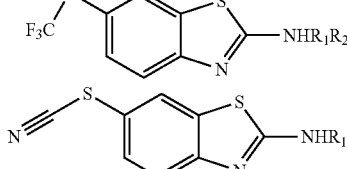

-continued

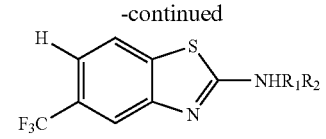
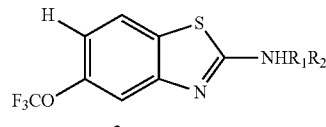
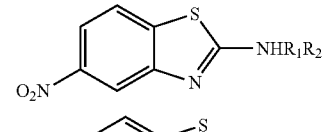
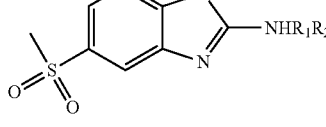
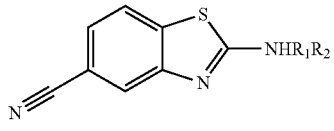
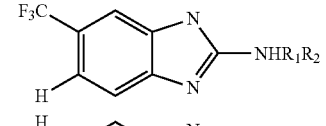
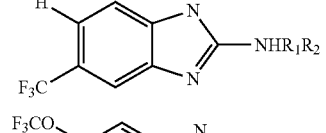
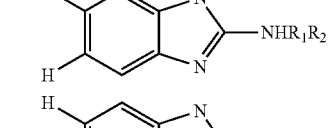
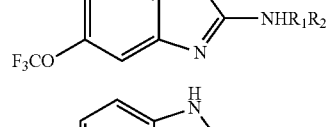
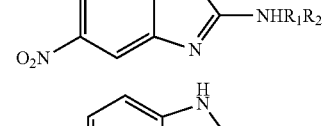
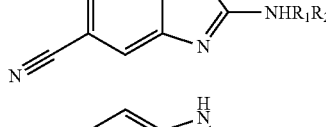
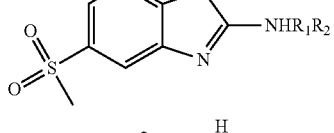
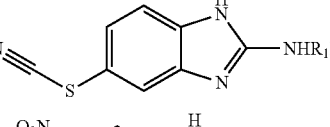
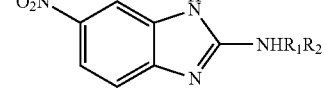

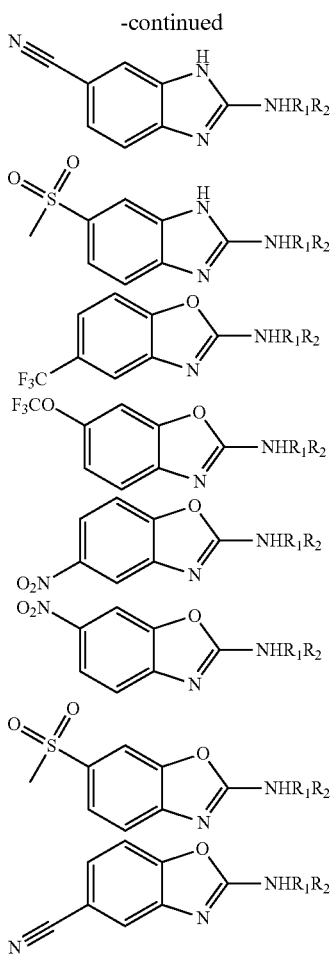

wherein $R_1$ or $R_2$ are as above defined; and with the proviso that when $W_1$ or $W_2$ is N, the compound of Formula (A) is not one of the following compounds:

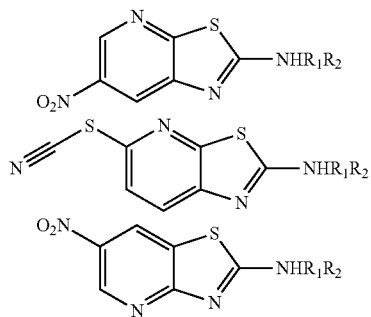

wherein $R_1$ or $R_2$ are as above defined.

In a further aspect, the invention relates to pharmaceutical compositions each comprising an effective amount of at least one compound of Formula (A) or a pharmaceutically acceptable salt of a compound of Formula (A). Pharmaceutical compositions according to the invention may further comprise at least one pharmaceutically acceptable excipient, carrier, adjuvant, solvent, support or a combination thereof.

In another aspect, the invention is directed to a method of treating a subject suffering from, inter alia, a neurological or psychiatric disease or disorder or medical condition of a cancer, that is mediated by dysfunctional glutamate transmission, comprising administering to the subject in need of such treatment an effective amount of at least one compound of Formula (A) or a pharmaceutically acceptable salt of a compound of Formula (A), or comprising administering to the subject in need of such treatment an effective amount of a pharmaceutical composition comprising an effective amount of at least one compound of Formula (A) or a pharmaceutically acceptable salt of a compound of Formula (A).

An aspect of the present invention concerns the use of compound of Formula (A) for the preparation of a medicament used in the treatment, prevention, inhibition or elimination of a neurological and psychiatric disorder or disease, which medicament further comprises therapeutically effective amounts of one or more, optional, adjunctive active ingredients, which adjunctive active ingredient comprises an antipsychotic, an atypical antipsychotic, an antiepileptic, an anti-Parkinson's disease drug, an anti-amyotrophic lateral sclerosis drug, anti-pain drug, anti-multiple sclerosis drug, spinal cord injury or a combination thereof, selected from the group consisting of riluzole, amitriptyline, desipramine, mirtazapine, bupropion, reboxetine, fluoxetine, trazodone, sertraline, duloxetine, fluvoxamine, milnacipran, levomilnacipran, desvenlafaxine, vilazodone, venlafaxine, dapoxetine, nefazodone, femoxetine, clomipramine, citalopram, escitalopram, paroxetine, lithium carbonate, buspirone, olanzapine, quetiapine, risperidone, ziprasidone, aripiprazole, perospirone, clozapine, modafinil, mecamylamine, cabergoline, adamantane, imipramine, pramipexole, thyroxine, dextromethorphan, quinidine, naltrexone, samidorphan, buprenorphine, melatonin, alprazolam, pipamperone, vestipitant, perphenazine, midazolam, triazolam, estazolam, diazepam, flurazepam, nitrazepam, clonazepam, temazepam, flunitrazepam, oxazepam, zolpidem, zaleplon, zopiclone, eszopiclone, indiplon, tiagabine, gaboxadol, clomipramine, doxepin, chloral hydrate, haloperidol, chlorpromazine, carbamazepine, promethazine, lorazepam, hydroxyzine, aspirin, diphenhydramine, chlorpheniramine, lendormin, ramelteon, tasimelteon, agomelatine, mianserin, femoxetine, nabilone, doxepin, gabapentin, chlordiazepoxide, suvorexant, Xuezang Guben or a combination thereof.

An aspect of the present invention concerns the use of compound of Formula (A) for the preparation of a medicament used in the treatment, prevention, inhibition or elimination of a cancer, which medicament further comprises therapeutically effective amounts of one or more, optional, adjunctive active ingredients, which adjunctive active ingredient comprises a chemotherapeutic agent, selected from the group consisting of: cytotoxic agent, cisplatin, doxorubicin, taxotere, taxol, etoposide, irinotecan, camptostar, topotecan, paclitaxel, docetaxel, the epothilones, tamoxifen, 5-fluorouracil, methoxtrexate, temozolomide, cyclophosphamide, SCH 66336, tipifarnib (Zarnestra®), R115777, L778,123, BMS 214662, Iressa®, Tarceva®, C225, GLEEVEC®, Intron®, Peg-Intron®, aromatase combinations, ara-C, adriamycin, ercept, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN®), Pentostatine, Vinblastine, Vincristine, Vindesine, Bleomycin, Dactinomycin, Daunorubicin, Epirubicin, Idarubicin, Mithramycin™, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrol acetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Fulvestrant, Exemestane, Ifosfomide, Rituximab, Campath, leucovorin, and dexamethasone, bicalutamide, carboplatin, chlorambucil, letrozole, megestrol, and valrubicin, or a combination thereof.

Another aspect of the present invention concerns the use of a compound of Formula (A) for the preparation of a medicament used in the treatment, prevention, inhibition or elimination of a disorder or disease or medical condition in a patient by modulating glutamate transmission in said patient, wherein said disorder or disease or medical condition is selected from the group consisting of: glioma, breast cancer, melanoma; amyotrophic lateral sclerosis (ALS), chronic neuropathy pain, multiple sclerosis, ataxia, Parkinson's, Huntington's, Tourette syndrome, epilepsy, dystonia, Fragile X syndrome, disorders resulting from traumatic brain/spinal cord injuries, disorders resulting from cerebral ischemia; depression, anxiety, bipolar disorder, schizophrenia, obsessive compulsive disorder, autism, alcohol/drug addiction; vascular and Alzheimer's dementia, glaucoma induced optical neuropathy and attention deficit/hyperactive disorder (ADHD).

In yet another aspect of the present invention, the compounds of Formula (A) and pharmaceutically acceptable salts thereof are useful as modulators of glutamate transmission. Thus, the invention is directed to a method for modulating glutamate transmission in a subject, comprising exposing the subject to an effective amount of at least one compound of Formula (A) or a pharmaceutically acceptable salt of a compound of Formula (A).

In yet another aspect, the present invention is directed to methods of making compounds of Formula (A) and pharmaceutically acceptable salts thereof.

In certain embodiments of the compounds, pharmaceutical compositions, and methods of the invention, the compound of Formula (A) is a compound selected from those species described or exemplified in the detailed description below, or is a pharmaceutically acceptable salt of such a compound.

Another preferred embodiment, the present invention is directed to methods of preparing pharmaceutical compositions each comprising an effective amount of at least one compound of Formula (A) or a pharmaceutically acceptable salt of a compound of Formula (A). Pharmaceutical compositions according to the invention may further comprise at least one pharmaceutically acceptable excipient, carrier, adjuvant, solvent, support or a combination thereof.

If formulated as a fixed dose, such combination products employ the compounds of this invention within the dosage range described herein (or as known to those skilled in the art) and the other pharmaceutically active agents or treatments within its dosage range. For example, the CDC2 inhibitor olomucine has been found to act synergistically with known cytotoxic agents in inducing apoptosis (*J. Cell Sci.*, (1995) 108, 2897). The compounds of the invention may also be administered sequentially with known anticancer or cytotoxic agents when a combination formulation is inappropriate. In any combination treatment, the invention is not limited in the sequence of administration; compounds of Formula (A) may be administered either prior to or after administration of the known anticancer or cytotoxic agent. For example, the cytotoxic activity of the cyclin-dependent kinase inhibitor flavopiridol is affected by the sequence of administration with anticancer agents (*Cancer Research*, (1997) 57, 3375). Such techniques are within the skills of persons skilled in the art as well as attending physicians.

Any of the aforementioned methods may be augmented by administration of fluids (such as water), loop diuretics, one or more of a chemotherapeutic or antineoplastic agent, such as leucovorin and fluorouracil, and an adjunctive chemotherapeutic agent (such as filgrastim and erythropoietin), or any combination of the foregoing.

Yet another embodiment is a method for administering a compound of the instant invention to a subject (e.g., a human) in need thereof by administering to the subject the pharmaceutical formulation of the present invention.

Yet another embodiment is a method of preparing a pharmaceutical formulation of the present invention by mixing at least one pharmaceutically acceptable compound of the present invention, and, optionally, one or more pharmaceutically acceptable additives or excipients.

For preparing pharmaceutical compositions from the compounds described by this invention, inert, pharmaceutically acceptable carriers can be either solid or liquid. Solid form preparations include powders, tablets, dispersible granules, capsules, beads, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 500 mg, more preferably from about 1 mg to about 250 mg, still more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 200 mg/day, preferably 10 mg/day to 100 mg/day, in one to two divided doses.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limiting in nature. These aspects and other aspects and additional embodiments, features, and advantages of the invention will be apparent from the following detailed description and through practice of the invention.

BRIEF DESCRIPTION OF THE DRAWINGS

These and other aspects and advantages of embodiments of the present disclosure will become apparent and more readily appreciated from the following descriptions made with reference the accompanying schemes and drawings, in which.

DETAILED DESCRIPTION

Figure 1B:
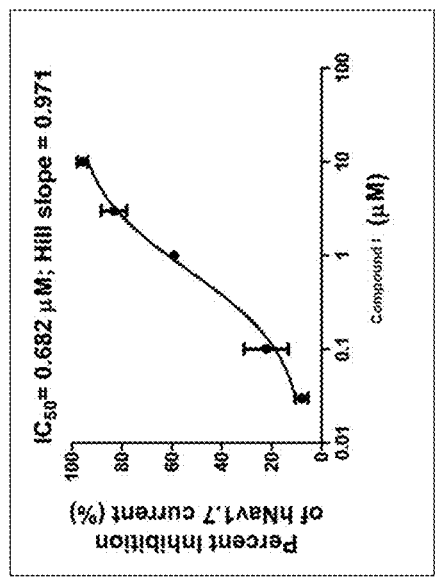
FIGS. 1A and 1B show the inhibitory effect of Compound I on hNav1.2/1.7 channel.

For the sake of brevity, the disclosures of the publications cited in this specification, including patents and patent applications, are herein incorporated by reference in their entirety.

Most chemical names were generated using IUPAC nomenclature herein. Some chemical names were generated using different nomenclatures or alternative or commercial names known in the art. In the case of conflict between names and structures, the structures prevail.

Reference will now be made in detail to certain embodiments of the invention, examples of which are illustrated in the accompanying structures and formulas. The invention is intended to cover all alternatives, modifications and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

Unless defined otherwise, all technical and scientific terms used herein have the same meaning as are commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry" by Michael B. Smith and Jerry March, John Wiley & Sons, New York: 2007, the entire contents of which are hereby incorporated by reference.

As used above, and throughout this disclosure, the following terms, unless otherwise indicated, shall be understood to have the following meanings. If a definition is missing, the conventional definition as known to one skilled in the art controls. If a definition provided herein conflicts or is different from a definition provided in any cited publication, the definition provided herein controls.

As used herein, the terms "including", "containing", and "comprising" are used in their open, non-limiting sense.

As used herein, the singular forms "a", "an", and "the" include plural referents unless the context clearly dictates otherwise.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

As used herein, "alkyl" refers to a saturated, straight- or branched-chain hydrocarbon group having from 1 to 12 carbon atoms. Representative alkyl groups include, but are not limited to, methyl, ethyl, n-propyl, isopropyl, 2-methyl- 1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl, and the like, and longer alkyl groups, such as heptyl, octyl, and the like. As used herein, "lower alkyl" means an alkyl having from 1 to 6 carbon atoms.

The term "alkylamino" as used herein denotes an amino group as defined herein wherein one hydrogen atom of the amino group is replaced by an alkyl group as defined herein. Aminoalkyl groups can be defined by the following general formula —NH-alkyl. This general formula includes groups of the following general formulae: —NH—$C_1$-$C_{10}$ alkyl and —NH—$C_1$-$C_6$ alkyl. Examples of aminoalkyl groups include, but are not limited to aminomethyl, aminoethyl, aminopropyl, aminobutyl.

The term "dialkylamino" as used herein denotes an amino group as defined herein wherein two hydrogen atoms of the amino group are replaced by alkyl groups as defined herein. Diaminoalkyl groups can be defined by the following general formula —N(alkyl)$_2$, wherein the alkyl groups can be the same or can be different and can be selected from alkyls as defined herein, for example $C_1$-$C_{10}$ alkyl or $C_1$-$C_6$ alkyl.

The term "alkoxy" as used herein includes —O-(alkyl), wherein alkyl is defined above.

As used herein, "alkoxyalkyl" means -(alkylenyl)-O-(alkyl), wherein each "alkyl" is independently an alkyl group defined above.

The term "amino" as used herein refers to an —NH$_2$ group.

"Aryl" means a mono-, bi-, or tricyclic aromatic group, wherein all rings of the group are aromatic. For bi- or tricyclic systems, the individual aromatic rings are fused to one another. Exemplary aryl groups include, but are not limited to, phenyl, naphthalene, and anthracene.

"Aryloxy" as used herein refers to an —O-(aryl) group, wherein aryl is defined as above.

"Arylalkyl" as used herein refers to an -(alkylenyl)-(aryl) group, wherein alkylenyl and aryl are as defined above. Non-limiting examples of arylalkyls comprise a lower alkyl group. Non-limiting examples of suitable arylalkyl groups include benzyl, 2-phenethyl, and naphthalenylmethyl.

"Arylalkoxy" as used herein refers to an —O-(alkylenyl)-aryl group wherein alkylenyl and aryl are as defined above.

The term "cyano" as used herein means a substituent having a carbon atom joined to a nitrogen atom by a triple bond.

The term "cyanoalkyl" denotes an alkyl group as defined above wherein a hydrogen atom of the alkyl group is replaced by a cyano (—CN) group. The alkyl portion of the cyanoalkyl group provides the connection point to the remainder of the molecule.

The term "deuterium" as used herein means a stable isotope of hydrogen having one proton and one neutron.

The term "halogen" as used herein refers to fluorine, chlorine, bromine, or iodine. The term "halo" represents chloro, fluoro, bromo, or iodo.

The term "haloalkyl" denotes an alkyl group as defined above wherein one or more, for example one, two, or three of the hydrogen atoms of the alkyl group are replaced by a halogen atom, for example fluoro, bromo, or chloro, in particular fluoro. Examples of haloalkyl include, but are not limited to, monofluoro-, difluoro-, or trifluoro-methyl, -ethyl or -propyl, for example, 3,3,3-trifluoropropyl, 2-fluoroethyl, 2,2,2-trifluoroethyl, fluoromethyl, difluoromethyl, or trifluoromethyl, or bromoethyl or chloroethyl. Similarly, the term "fluoroalkyl" refers to an alkyl group as defined above substituted with one or more, for example one, two, or three fluorine atoms.

The term "haloalkoxy" as used herein refers to an —O-(haloalkyl) group wherein haloalkyl is defined as above. Exemplary haloalkoxy groups are bromoethoxy, chloroethoxy, trifluoromethoxy and 2,2,2-trifluoroethoxy.

The term "hydroxy" means an —OH group.

The term "hydroxyalkyl" denotes an alkyl group that is substituted by at least one hydroxy group, for example, one, two or three hydroxy group(s). The alkyl portion of the hydroxyalkyl group provides the connection point to the remainder of a molecule. Examples of hydroxyalkyl groups include, but are not limited to, hydroxymethyl, hydroxyethyl, 1-hydroxypropyl, 2-hydroxyisopropyl, 1,4-dihydroxybutyl, and the like.

The term "oxo" means an =O group and may be attached to a carbon atom or a sulfur atom. The term "N-oxide" refers to the oxidized form of a nitrogen atom.

As used herein, the term "cycloalkyl" refers to a saturated or partially saturated, monocyclic, fused polycyclic, bridged polycyclic, or spiro polycyclic carbocycle having from 3 to 12 ring carbon atoms. A non-limiting category of cycloalkyl groups are saturated or partially saturated, monocyclic carbocycles having from 3 to 6 carbon atoms. Illustrative examples of cycloalkyl groups include, but are not limited to, the following moieties:

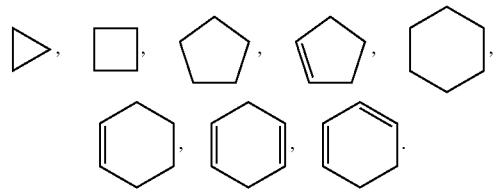

The term "cycloalkoxy" refers to a —O-(cycloalkyl) group.

As used herein, the term "heteroaryl" refers to a monocyclic, or fused polycyclic, aromatic heterocycle having from three to 15 ring atoms that are selected from carbon, oxygen, nitrogen, selenium and sulfur. Suitable heteroaryl groups do not include ring systems that must be charged to be aromatic, such as pyrylium. Some suitable 5-membered heteroaryl rings (as a monocyclic heteroaryl or as part of a polycyclic heteroaryl) have one oxygen, sulfur, or nitrogen atom, or one nitrogen plus one oxygen or sulfur, or 2, 3, or 4 nitrogen atoms. Some suitable 6-membered heteroaryl rings (as a monocyclic heteroaryl or as part of a polycyclic heteroaryl) have 1, 2, or 3 nitrogen atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The term "bicyclic heteroaryl" refers to a heteroaryl as defined above, having two constituent aromatic rings, wherein the two rings are fused to one another and at least one of the rings is a heteroaryl as defined above. Bicyclic heteroaryls include bicyclic heteroaryl groups comprising 1, 2, 3, or 4 heteroatom ring members and are unsubstituted or substituted with one or more substituents selected from the group consisting of amino and halo; and wherein one or more N ring members of said heteroaryl is optionally an N-oxide. Bicyclic heteroaryls also include 8-, 9-, or 10-membered bicyclic heteroaryl groups. Bicyclic heteroaryls also include 8-, 9-, or 10-membered bicyclic heteroaryl groups that have 1, 2, 3 or 4 heteroatom ring members and that are unsubstituted or substituted with one or more substituents selected from the group consisting of amino and halo; and wherein one or more N ring members of said heteroaryl is optionally an N-oxide. Illustrative examples of bicyclic heteroaryls with respect to the present invention include, but are not limited to:

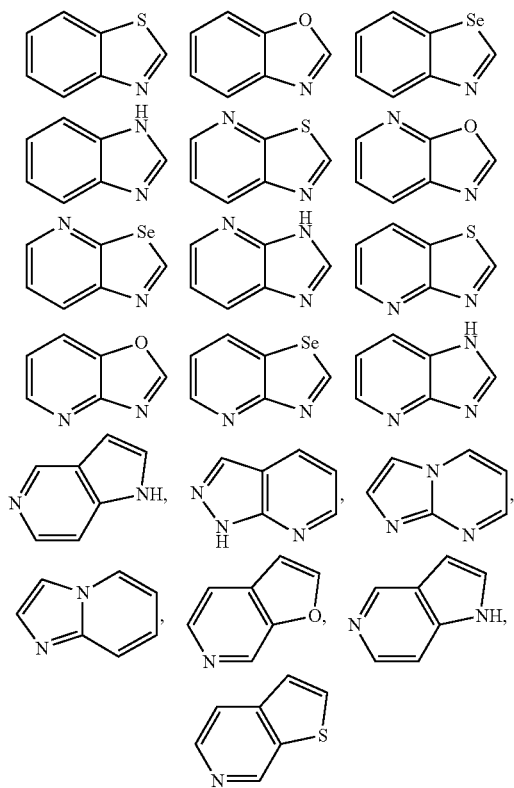

Those skilled in the art will recognize that the species of heteroaryl, and cycloalkyl groups listed or illustrated above are not exhaustive, and that additional species within the scope of these defined terms may also be selected.

As described herein, compounds disclosed herein may optionally be substituted with one or more substituents, or as exemplified by particular classes, subclasses, and species of the invention.

As used herein, the term "substituted" means that the specified group or moiety bears one or more suitable substituents. As used herein, the term "unsubstituted" means that the specified group bears no substituents. As used herein, the term "optionally substituted" means that the specified group is unsubstituted or substituted by the specified number of substituents. Where the term "substituted" is used to describe a structural system, the substitution is meant to occur at any valency-allowed position on the system.

As used herein, the expression "one or more substituents" denotes one to maximum possible number of substitution(s) that can occur at any valency-allowed position on the system. In a certain embodiment, one or more substituent means 1, 2, 3, 4, or 5 substituents. In another embodiment, one or more substituent means 1, 2, or 3 substituents.

Any atom that is represented herein with an unsatisfied valence is assumed to have the sufficient number of hydrogen atoms to satisfy the atom's valence.

When any variable (e.g., alkyl, alkylenyl, heteroaryl, $R_1$, $R_2$, or $R_a$) appears in more than one place in any formula or description provided herein, the definition of that variable on each occurrence is independent of its definition at every other occurrence.

Numerical ranges, as used herein, are intended to include sequential whole numbers. For example, a range expressed as "from 0 to 4" or "0-4" includes 0, 1, 2, 3 and 4, while a range expressed as "10-20%" includes 10%, 11%, 12%, 13%, 14%, 15%, 16%, 17%, 18%, 19% and 20%. Similarly, numerical ranges are also intended to include sequential fractional integers. For example, a range expressed as "1-2%" would include 1.0%, 1.1%, 1.2%, 1.3%, 1.4%, 1.5%, 1.6%, 1.7%, 1.8%, 1.9% and 2.0%.

When a multifunctional moiety is shown, the point of attachment to the core is indicated by a line or hyphen. For example, aryloxy- refers to a moiety in which an oxygen atom is the point of attachment to the core molecule while aryl is attached to the oxygen atom.

As used herein, the term "subject" encompasses mammals and non-mammals. Examples of mammals include, but are not limited to, any member of the Mammalian class: humans; non-human primates such as chimpanzees, and other apes and monkey species; farm animals such as cattle, horses, sheep, goats, swine; domestic animals such as rabbits, dogs, and cats; and laboratory animals including rodents, such as rats, mice and guinea pigs, and the like. Examples of non-mammals include, but are not limited to, birds, fish and the like. In one embodiment of the present invention, the mammal is a human.

"Patient" includes both human and animals.

The term "inhibitor" refers to a molecule such as a compound, a drug, an enzyme activator, or a hormone that blocks or otherwise interferes with a particular biologic activity.

The term "modulator" refers to a molecule, such as a compound of the present invention, that increases or decreases, or otherwise affects the activity of a given protein, receptor and/or ion channels.

The terms "effective amount" or "therapeutically effective amount" refer to a sufficient amount of the agent to provide the desired biological result. That result can be reduction and/or alleviation of the signs, symptoms, or causes of a disease or medical condition, or any other desired alteration of a biological system. For example, an "effective amount" for therapeutic use is the amount of a compound, or of a composition comprising the compound, that is required to provide a clinically relevant change in a disease state, symptom, or medical condition. An appropriate "effective" amount in any individual case may be determined by one of ordinary skill in the art using routine experimentation. Thus, the expression "effective amount" generally refers to the quantity for which the active substance has a therapeutically desired effect.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

As used herein, the terms "administration of" and "administering a" compound should be understood to mean providing a compound of the invention, pharmaceutical composition comprising a compound or a prodrug of a compound of the invention to an individual in need thereof. It is recognized that one skilled in the non-limiting art can treat a patient presently afflicted with neurological and psychiatric disorders or by prophylactically treat a patient afflicted with the disorders with an effective amount of the compound of the present invention.

The term "composition" as used herein is intended to encompass a product comprising the specified ingredients in the specified amounts, as well as any product which results, directly or indirectly, from combinations of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from a combination, complexation or aggregation of any two or more of the ingredients, or from the other types of reactions or interactions such as to cause the dissociation of one or more of the ingredients. Accordingly, the pharmaceutical compositions of the present invention encompass any composition made by mixing a compound of the present invention and a pharmaceutically acceptable carrier.

Any formula given herein is intended to represent compounds having structures depicted by the structural formula as well as certain variations or forms. For example, compounds of any formula given herein may have asymmetric or chiral centers and therefore exist in different stereoisomeric forms. All stereoisomers, including optical isomers, enantiomers, and diastereomers, of the compounds of the general formula, and mixtures thereof, are considered to fall within the scope of the formula. Furthermore, certain structures may exist as geometric isomers (i.e., cis and trans isomers), as tautomers, or as atropisomers. All such isomeric forms, and mixtures thereof, are contemplated herein as part of the present invention. Thus, any formula given herein is intended to represent a racemate, one or more enantiomeric forms, one or more diastereomeric forms, one or more tautomeric or atropisomeric forms, and mixtures thereof.

"Stereoisomer" refers to compounds which have identical chemical constitution, but differ with regard to the arrangement of the atoms or groups in space. Stereoisomers include enantiomer, diastereomers, conformer (rotamer), geometric (cis/trans) isomer, atropisomer etc.

"Chiral" refers to molecules which have the property of non-superimposability of the mirror image partner, while the term "achiral" refers to molecules which are superimposable on their mirror image partner.

"Enantiomers" refers to two stereoisomers of a compound which are non-superimposable mirror images of one another.

"Diastereomer" refers to a stereoisomer with two or more centers of chirality and whose molecules are not mirror images of one another. Diastereomers have different physical properties, e.g., melting points, boiling points, spectral properties or biological activities. A mixture of diastereomers may be separated under high resolution analytical procedures such as electrophoresis and chromatography such as HPLC.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

Many organic compounds exist in optically active forms, i.e., they have the ability to rotate the plane of polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, a cycloalkyl substituent may have a cis- or trans-configuration relative to another substituent of the same cycloalkyl frame.

Any resulting mixtures of stereoisomers can be separated on the basis of the physicochemical differences of the constituents, into the pure or substantially pure geometric isomers, enantiomers, diastereomers, for example, by chromatography and/or fractional crystallization. Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); *Principles of Asymmetric Synthesis* (2nd Ed. Robert E. Gawley, Jeffrey Aubé, Elsevier, Oxford, U K, 2012); Eliel, E. L. Stereochemistry of Carbon Compounds (McGraw-Hill, NY, 1962);

Wilen, S. H. Tables of Resolving Agents and Optical Resolutions p. 268 (E. L. Eliel, Ed., Univ. of Notre Dame Press, Notre Dame, Ind. 1972); Chiral Separation Techniques: A Practical Approach (Subramanian, G. Ed., Wiley-VCH Verlag GmbH & Co. KGaA, Weinheim, Germany, 2007).

Diastereomeric mixtures may be separated into their individual diastereomers on the basis of their physical chemical differences by methods well known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride, or formation of a mixture of diastereomeric salts), separating the diastereomers and converting (e.g., hydrolyzing or de-salting) the individual diastereomers to the corresponding pure enantiomers. Enantiomers may also be separated by use of chiral HPLC column.

The compounds of the invention can form pharmaceutically acceptable salts, which are also within the scope of this invention. A "pharmaceutically acceptable salt" refers to a salt of a free acid or base of a compound of Formula I that is non-toxic, is physiologically tolerable, is compatible with the pharmaceutical composition in which it is formulated, and is otherwise suitable for formulation and/or administration to a subject. Reference to a compound herein is understood to include reference to a pharmaceutically acceptable salt of said compound unless otherwise indicated.

Compound salts include acidic salts formed with inorganic and/or organic acids, as well as basic salts formed with inorganic and/or organic bases. In addition, where a given compound contains both a basic moiety, such as, but not limited to, a pyridine or imidazole, and an acidic moiety, such as, but not limited to, a carboxylic acid, one of skill in the art will recognize that the compound may exist as a zwitterion ("inner salt"); such salts are included within the term "salt" as used herein. Salts of the compounds of the invention may be prepared, for example, by reacting a compound with an amount of a suitable acid or base, such as an equivalent amount, in a medium such as one in which the salt precipitates or in an aqueous medium followed by lyophilization.

Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate ("mesylate"), ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counter ion.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, tert-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Additionally, acids and bases which are generally considered suitable for the formation of pharmaceutically useful salts from pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, MD, available from FDA). These disclosures are incorporated herein by reference thereto.

Additionally, any compound described herein is intended to refer also to any unsolvated form, or a hydrate, solvate, or polymorph of such a compound, and mixtures thereof, even if such forms are not listed explicitly. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of a crystalline solid. "Solvate" encompasses both solution-phase and isolatable solvates. Suitable solvates include those formed with pharmaceutically acceptable solvents such as water, ethanol, and the like. In some embodiments, the solvent is water and the solvates are hydrates.

One or more compounds of the invention may optionally be converted to a solvate. Methods for the preparation of solvates are generally known. Thus, for example, M. Caira et al., J. Pharmaceutical Sci., 93(3), 601-611 (2004), describes the preparation of the solvates of the antifungal fluconazole in ethyl acetate as well as from water. Similar preparations of solvates, hemisolvate, hydrates, and the like are described by E. C. van Tonder et al, *AAPS PharmSciTech.*, 5(1), article 12 (2004); and A. L. Bingham et al, Chem. Commun., 603-604 (2001). A typical, non-limiting process involves dissolving the compound of the invention in a suitable amount of the solvent (organic solvent or water or a mixture thereof) at a higher than ambient temperature, and cooling the solution at a rate sufficient to form crystals which are then isolated by standard methods. Analytical techniques such as, for example, infrared spectroscopy, show the presence of the solvent (or water) in the crystals as a solvate (or hydrate).

The present invention also relates to pharmaceutically active metabolites of compounds of Formula (A), and uses of such metabolites in the methods of the invention. A "pharmaceutically active metabolite" means a pharmacologically active product of metabolism in the body of a compound of Formula (A) or salt thereof. Active metabolites of a compound may be determined using routine techniques known or available in the art. See, e.g., Bertolini et al., *J Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (for example with $^{14}C$), reaction kinetic studies (with, for example $^2H$ or $^3H$), detection or imaging techniques [such as positron emission tomography (PET) or single-photon emission computed tomography (SPECT) including drug or substrate tissue distribution assays, or in radioactive treatment of patients. In particular, an $^{18}F$ or $^{11}C$ labeled compound may be particularly suitable for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

The use of the terms "salt," "solvate," "polymorph," and the like, with respect to the compounds described herein is intended to apply equally to the salt, solvate, and polymorph forms of enantiomers, stereoisomers, rotamers, tautomers, atropisomers, and racemates of the compounds of the invention.

The present invention relates to particular molecules and pharmaceutically acceptable salts or isomers thereof. The invention further relates to molecules which are useful in modulating dysfunctional glutamate transmission and pharmaceutically acceptable salts, solvates, esters, or isomers thereof.

The invention is directed to compounds as described herein and pharmaceutically acceptable salts, solvates, esters, or isomers thereof, and pharmaceutical compositions comprising one or more compounds as described herein and pharmaceutically acceptable salts or isomers thereof. One aspect of this invention is the provision of compounds, compositions, kits, and antidotes for modulating glutamate transmission in mammals having a compound of the Formula (A):

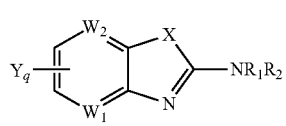

(A)

wherein,

X is NH, O, S or Se;

$W_1$ or $W_2$ is CH or N, provided that $W_1$ and $W_2$ are not both N;

$R_1$ and $R_2$ are the same, or they are different, and are independently selected from the group consisting of: Hydrogen and $GR^a$, wherein G is absent, —C(O)— or —C(O)O— and $R^a$ is a saturated straight or branched alkyl of from one to four carbon atoms, or a saturated cycloalkyl of from three to six carbon atoms, provided that $R_1$ and $R_2$ are not both $GR^a$, wherein G is not absent;

$Y_q$ is selected from the group consisting of hydrogen, deuterium, $SF_5$, $CF_3$, $OCF_3$, $SCF_3$, $S(O)CF_3$, $S(O)_2 CF_3$, CN, SCN, $S(O)CH_3$, $S(O)_2CH_3$, $NO_2$, and wherein q is 1 or 2; provided that when q is 2, $Y_1$ and $Y_2$ can be the same, or different, and they are not both hydrogen, or both deuterium, or one each of hydrogen and deuterium;

or a pharmaceutically acceptable salt thereof, and with the proviso that when $W_1$ and $W_2$ are CH, the compound of Formula (A) is not one of the following compounds:

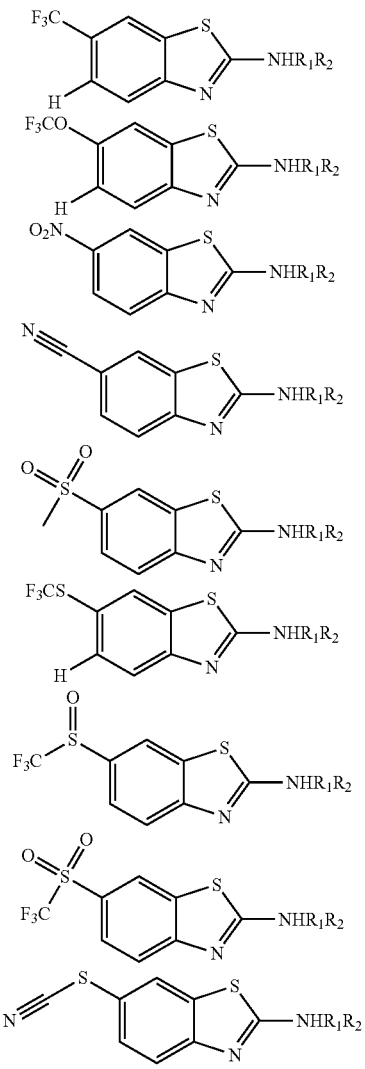

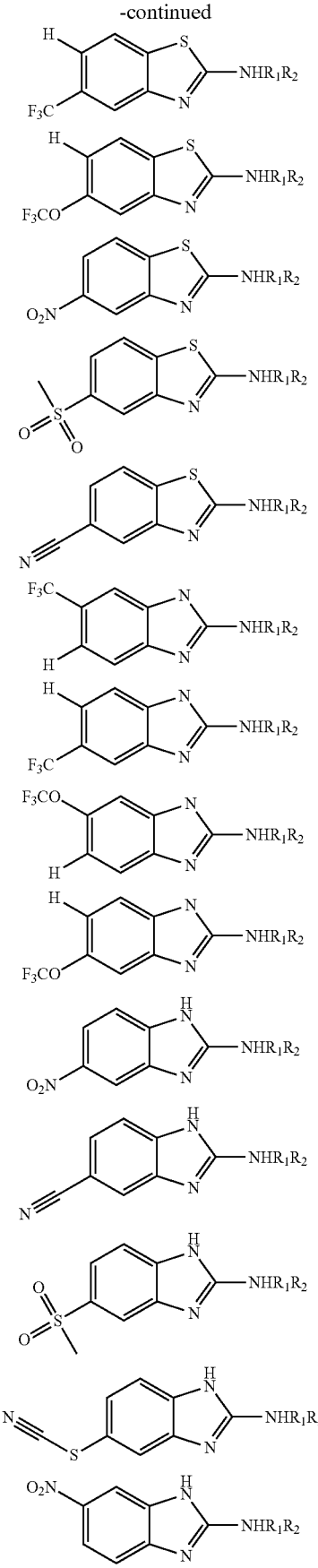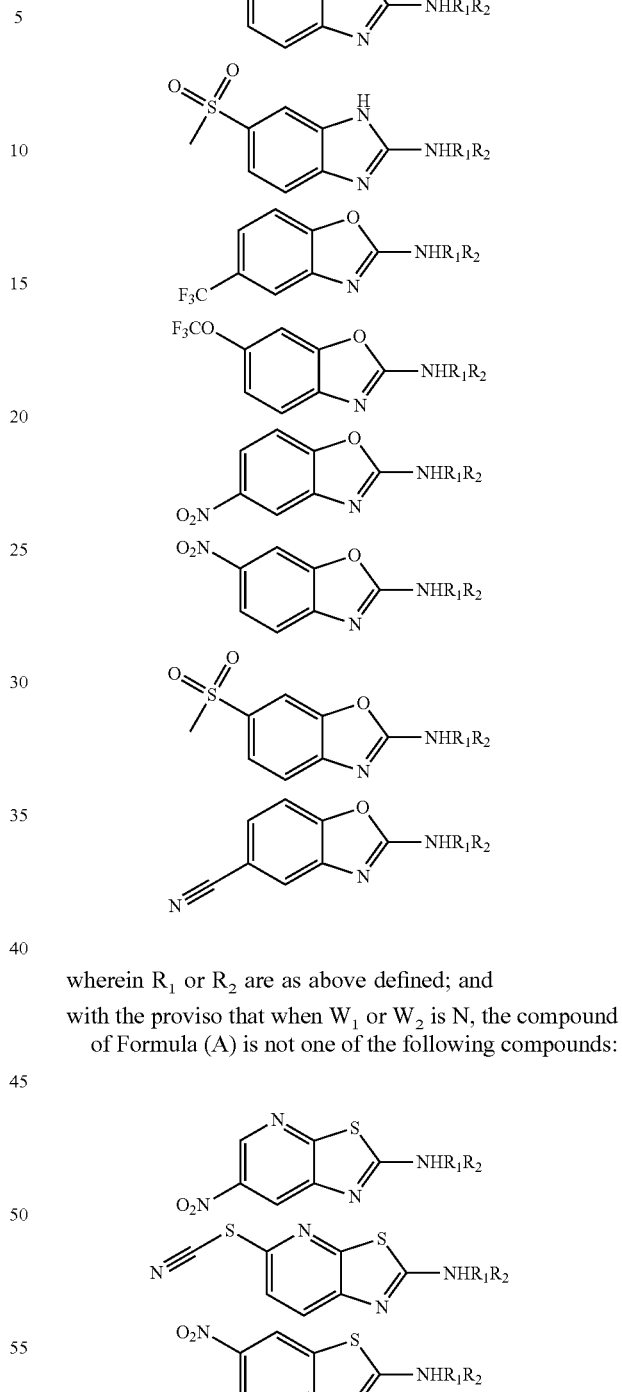

wherein $R_1$ or $R_2$ are as above defined; and with the proviso that when $W_1$ or $W_2$ is N, the compound of Formula (A) is not one of the following compounds:

wherein $R_1$ or $R_2$ are as above defined.

In some embodiments, in which compounds having the general Formula (A), X is NH or O or S or Se. In other embodiments, $W_1$ or $W_2$ is N provided that $W_1$ and $W_2$ are not both N. In yet other embodiments, $W_1$ or $W_2$ is CH. In other embodiments, the core bicyclic heteroaryl is selected from the group consisting of:

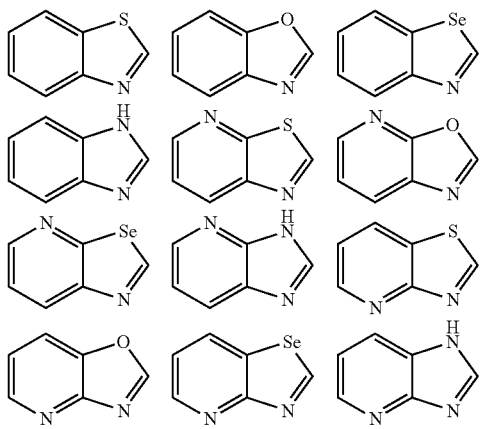

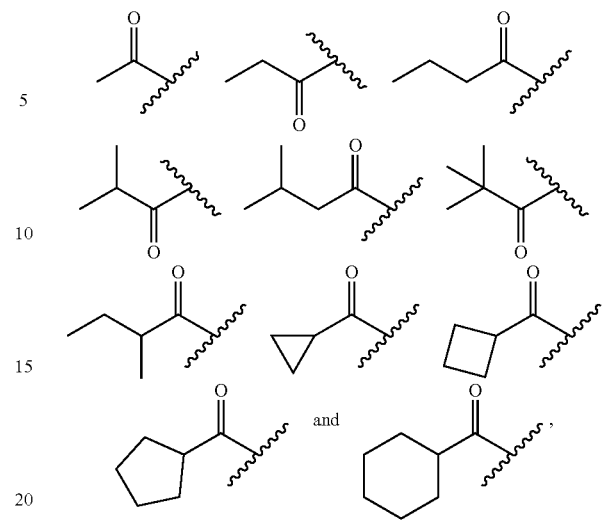

In still other embodiments, in which compounds having the general Formula (A), $Y_q$ is selected from the group consisting of hydrogen, deuterium, $SF_5$, $CF_3$, $OCF_3$, $SCF_3$, $S(O)CF_3$, $S(O)_2CF_3$, CN, SCN, $S(O)CH_3$, $S(O)_2CH_3$, $NO_2$, where q is 1 or 2, but provided that when q is 2, $Y_1$ and $Y_2$ can be the same, or different, and they are not both hydrogen, or both deuterium, or one each of hydrogen and deuterium.

In some embodiments, in which compounds having the general Formula (A), $R_1$ and $R_2$ are the same, or they are different, and are independently selected from the group consisting of: hydrogen and $GR^a$, wherein G is absent, —C(O)— or —C(O)O— and $R^a$ is a saturated straight or branched alkyl of from one to four carbon atoms, or a saturated cycloalkyl of from three to six carbon atoms, provided that $R_1$ and $R_2$ are not both $GR^a$, wherein G is not absent.

In some embodiments, in which compounds having the general Formula (A), $R_1$ or $R_2$ is $GR^a$, wherein G is absent and $R^a$ is a straight or branched alkyl of from one to four carbon atoms, and is selected from the group consisting of: —$CH_3$, —$CH_2CH_3$, —$CH_2CH_2CH_3$, —$CH(CH_3)_2$, —$CH_2CH_2CH_2CH_3$, —$CH_2CH(CH_3)_2$, and —$C(CH_3)_3$.

In some embodiments, in which compounds having the general Formula (A), $R_1$ or $R_2$ is $GR^a$, wherein G is absent and $R^a$ is a cycloalkyl of from three to six carbon atoms, and is selected from the group consisting of,

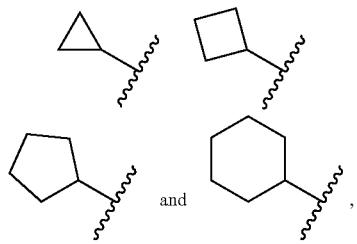

optionally, $R^a$ is substituted with $C_1$-$C_4$ alkyl.

In some embodiments, in which compounds having the general Formula (A), one of $R_1$ and $R_2$ is $GR^a$, wherein G is —C(O)— and $R^a$ is a saturated straight or branched alkyl of from one to four carbon atoms, or a saturated cycloalkyl of from three to six carbon atoms, and is selected from the group consisting of:

optionally, $R^a$ is substituted with $C_1$-$C_4$ alkyl.

In some embodiments, in which compounds having the general Formula (A), one of $R_1$ and $R_2$ is $GR^a$, wherein G is —C(O)O— and $R^a$ is a saturated straight or branched alkyl having from one to four carbon atoms, or a saturated cyclic alkyl having from three to six carbon atoms, and is selected from the group consisting of:

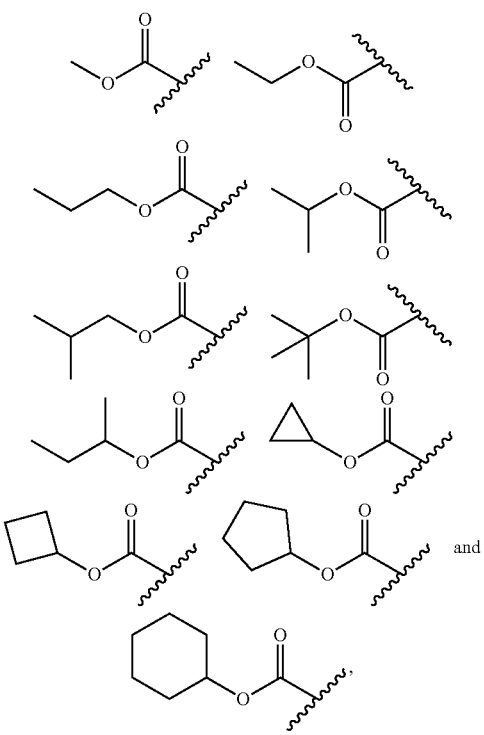

optionally, $R^a$ is substituted with $C_1$-$C_4$ alkyl.

In other embodiments, in which compounds having the general Formula (A), one of $R_1$ and $R_2$ is $GR^a$, wherein $R^a$ is selected from the group consisting of a saturated straight or branched alkyl of from one to four carbon atoms, and a saturated cycloalkyl of from three to six carbon atoms, wherein one or more of said carbon atoms is, optionally, an asymmetric atom.

An embodiment of the invention is the provision of a compound, where the various moieties are independently selected, $W_1$ and $W_2$ are CH, X is N, $Y_1$ is $SF_5$, $Y_2$ is H or D, and $R_1$ and $R_2$ are defined as above.

Another embodiment of the invention is the provision of a compound, where the various moieties are independently selected, $W_1$ and $W_2$ are CH, X is N, $Y_1$ and $Y_2$ are $SF_5$, and $R_1$ and $R_2$ are defined as above.

Another embodiment of the invention is the provision of a compound, where the various moieties are independently selected, $W_1$ and $W_2$ are CH, X is O, $Y_1$ is $SF_5$, $Y_2$ is H or D, and $R_1$ and $R_2$ are defined as above.

Another embodiment of the invention is the provision of a compound, where the various moieties are independently selected, $W_1$ and $W_2$ are CH, X is O, $Y_1$ and $Y_2$ are $SF_5$, and $R_1$ and $R_2$ are defined as above.

Another embodiment of the invention is the provision of a compound, where the various moieties are independently selected, $W_1$ and $W_2$ are CH, X is S, $Y_1$ is $SF_5$, $Y_2$ is H or D, and $R_1$ and $R_2$ are defined as above.

Another embodiment of the invention is the provision of a compound, where the various moieties are independently selected, $W_1$ and $W_2$ are CH, X is S, $Y_1$ and $Y_2$ are $SF_5$, and $R_1$ and $R_2$ are defined as above.

Another embodiment of the invention is the provision of a compound, where the various moieties are independently selected, $W_1$ and $W_2$ are CH, X is Se, $Y_1$ is $SF_5$, $Y_2$ is H or D, and $R_1$ and $R_2$ are defined as above.

Another embodiment of the invention is the provision of a compound, where the various moieties are independently selected, $W_1$ and $W_2$ are CH, X is Se, $Y_1$ and $Y_2$ are $SF_5$, and $R_1$ and $R_2$ are defined as above.

Another embodiment of the invention is the provision of a compound, where the various moieties are independently selected, $W_1$ and $W_2$ are CH, X is Se, $Y_1$ is selected from the group consisting of $CF_3$, $OCF_3$, $SCF_3$, $S(O)CF_3$, $S(O)_2CF_3$, CN, SCN, $S(O)CH_3$, $S(O)_2CH_3$, and $NO_2$, $Y_2$ is H or D, and $R_1$ and $R_2$ are defined as above.

Another embodiment of the invention is the provision of a compound, where the various moieties are independently selected, $W_1$ or $W_2$ is N, X is selected from the group consisting of N, O, S and Se, $Y_1$ is $SF_5$, $Y_2$ is H or D, and $R_1$ and $R_2$ are defined as above.

Another embodiment of the invention is the provision of a compound, where the various moieties are independently selected, $W_1$ or $W_2$ is N, X is selected from the group consisting of N, O, S and Se, $Y_1$ is $CF_3$, $Y_2$ is H or D, and $R_1$ and $R_2$ are defined as above.

Another embodiment of the invention is the provision of a compound, where the various moieties are independently selected, $W_1$ or $W_2$ is N, X is selected from the group consisting of N, O, S and Se, $Y_1$ is $OCF_3$, $Y_2$ is H or D, and $R_1$ and $R_2$ are defined as above.

Another embodiment of the invention is the provision of a compound, where the various moieties are independently selected, $W_1$ or $W_2$ is N, X is selected from the group consisting of N, O, S and Se, $Y_1$ is selected from the group consisting of $SCF_3$, $S(O)CF_3$, $S(O)_2CF_3$, CN, SCN, $S(O)CH_3$, $S(O)_2CH_3$, and $NO_2$, $Y_2$ is H or D, and $R_1$ and $R_2$ are defined as above.

In certain embodiments, the compound of Formula (A) is further illustrated by the following compound group consisting of:

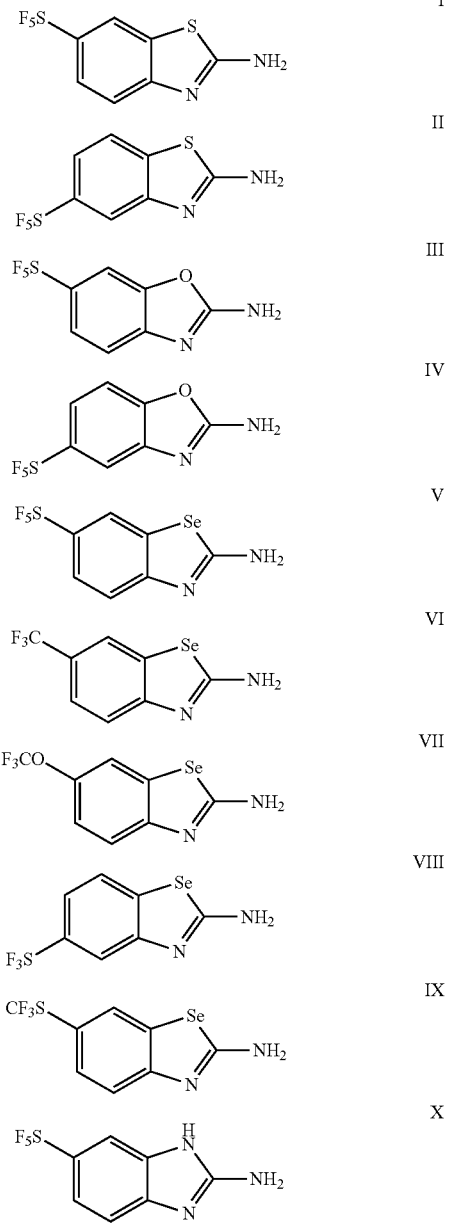

and pharmaceutically acceptable salts thereof.

An aspect of the present invention concerns compounds disclosed herein.

An aspect of the present invention concerns compounds which are or can be modulators of dysfunctional glutamate transmission.

An aspect of the present invention concerns the use of a modulator of dysfunctional glutamate transmission for the preparation of a medicament used in the treatment, prevention, inhibition or elimination of tumors.

An aspect of the present invention concerns the use of a modulator of dysfunctional glutamate transmission for the preparation of a medicament used in the treatment, prevention, inhibition or elimination of a disorder or disease or medical condition in a patient by modulating dysfunctional glutamate transmission in said patient, wherein said disorder or disease or medical condition is selected from the group consisting of: glioma, breast cancer, melanoma; amyotrophic lateral sclerosis (ALS), chronic neuropathy pain, multiple sclerosis, ataxia, Parkinson's, Huntington's, Tourette syndrome, epilepsy, dystonia, Fragile X syndrome, disorders resulting from traumatic brain/spinal cord injuries, disorders resulting from cerebral ischemia; depression, anxiety, bipolar disorder, schizophrenia, obsessive compulsive disorder, autism, alcohol/drug addiction; vascular and Alzheimer's dementia, glaucoma induced optical neuropathy and attention deficit/hyperactive disorder (ADHD).

The present invention also describes one or more methods of synthesizing the compounds of the present invention.

The invention also describes one or more uses of the compounds of the present invention.

The invention also describes one or more uses of the compounds of the present invention with an adjunctive agent such as use with tumor necrosis factor (TNF), granulocyte colony-stimulating factor (GCSF) or other chemotherapeutic agents.

The present invention also describes one or more methods of preparing various pharmaceutical compositions comprising the compounds of the present invention.

The invention also describes one or more uses of the various pharmaceutical compositions of the present invention for the preparation of a medicament used in the treatment, prevention, inhibition or elimination of a disorder or disease or medical condition in a patient by modulating dysfunctional glutamate transmission in said patient.

The present invention provides a pharmaceutical composition comprising compounds of the present invention, e.g., example compounds. According to the specific examples of the present invention, the pharmaceutical composition can further comprise pharmaceutically acceptable excipient, carrier, adjuvant, solvent and a combination thereof.

The present invention provides a method of treating, preventing or ameliorating a disease or disorder, comprising administrating a safe and effective amount of a combination of drugs containing compounds of the invention and one or more therapeutic active agents. Among them, the combination of drugs comprises one or more additional drugs for treatment of neurological and psychiatric disorders and diseases of central nervous system.

Other drugs for treatment of neurological and psychiatric disorders and diseases of central nervous system include, but are not limited to: an antipsychotic, an atypical antipsychotic, an antiepileptic, an anti-Parkinson's disease drug, an anti-amyotrophic lateral sclerosis drug, anti-pain drug or any combination thereof.

The amount of the compound of the pharmaceutical composition disclosed herein refers to an amount which can be effectively detected to modulate dysfunctional glutamate transmission of biology samples and in a patient. The active ingredient may be administered to subjects in need of such treatment in dosage that will provide optimal pharmaceutical efficacy, which is not limited to the desired therapeutic effects, on the route of administration, and on the duration of the treatment. The dosage will vary from patient to patient depending upon the nature and severity of disease, the patient's weight, special diet then being followed by a patient, concurrent medication, and other factors which those skilled in the art will recognize. The quantity of active compound in a unit dose of preparation may be varied or adjusted from about 1 mg to about 1000 mg, preferably from about 1 mg to about 500 mg, more preferably from about 1 mg to about 250 mg, still more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 200 mg/day, preferably 10 mg/day to 100 mg/day, which may be administered in single or multiple doses. In yet another embodiment about 1 mg to 50 mg per patient per day.

It will also be appreciated that certain of the compounds of the present invention can exist in free form for treatment, or where appropriate, as a pharmaceutically acceptable derivative or a prodrug thereof. A pharmaceutically acceptable derivative includes pharmaceutically acceptable salts, esters, salts of such esters, or any other adduct or derivative which upon administration to a patient in need thereof provide, directly or indirectly, a compound as otherwise described herein, or an therapeutically effective metabolite or residue thereof.

The pharmaceutical compositions of the invention may be prepared and packaged in bulk form wherein a safe and effective amount of a compound of Formula (A) disclosed herein can be extracted and then given to the patient, such as with powders or syrups. Generally, dosage levels of between 0.0001 to 10 mg/kg of body weight daily are administered to the patient to obtain effective modulation of dysfunctional glutamate transmission. Alternatively, the pharmaceutical compositions of the invention may be prepared and packaged in unit dosage form wherein each physically discrete unit contains a safe and effective amount of a compound of Formula (A) disclosed herein. When prepared in unit dosage form, the pharmaceutical compositions of the invention commonly contain from about 0.5 mg to 1 g, or 1 mg to 700 mg, or 5 mg to 100 mg, or more preferably, 25 mg to 60 mg of the compound of the invention.

When the pharmaceutical compositions of the present invention also contain one or more other active ingredients, in addition to a compound of the present invention, the weight ratio of the compound of the present invention to the second active ingredient may be varied and depend upon the effective dose of each ingredient. Thus, for example, when a compound of the present invention is combined with another agent, the weight ratio of the compound of the present invention to the other agent will generally range from about 1000:1 to about 1:1000, such as about 200:1 to 1:200. Combinations of a compound of the present invention and other active ingredients will generally also be within the aforementioned range, but in each case, an effective dose of each active ingredient in the combination should be used.

"Pharmaceutically acceptable excipient" as used herein means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions. In addition, each excipient must of course be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are resources that are available to the skilled artisan that describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The pharmaceutical compositions of the invention are prepared using techniques and methods known to those skilled in the art. Some of the methods commonly used in the art are described in Remington's Pharmaceutical Sciences (Mack Publishing Company).

Therefore, another aspect of the present invention is related to a method for preparing a pharmaceutical composition. The pharmaceutical composition contains the compound disclosed herein and pharmaceutically acceptable excipient, carrier, adjuvant, vehicle or a combination thereof, the method comprises mixing various ingredients. The pharmaceutical composition containing the compound disclosed herein can be prepared for example at normal ambient temperature and pressure.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and ascorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

Where appropriate, dosage unit formulations for oral administration can be microencapsulated. The formulation can also be prepared to prolong or sustain the release as for example by coating or embedding particulate material in polymers, wax, or the like.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all above dosage forms.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80 and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a sterile vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In other aspect, the pharmaceutical composition of the invention is prepared to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In one embodiment, the invention is directed to a dosage form adapted for administration to a patient by inhalation as a dry powder. Dry powder compositions for delivery to the lung by inhalation typically comprise a compound disclosed herein or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (e.g. micronised) compound can be defined by a $D_{50}$ value of about 1 to about 10 microns (for example as measured using laser diffraction).

Aerosols may be formed by suspending or dissolving a compound disclosed herein or a pharmaceutically acceptable salt thereof in a liquified propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (A) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminum stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilizing agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilizing agents, suspending agents or preservatives.

Topical preparations may be administered via one or more applications per day to the affected area; over skin areas occlusive dressings may advantageously be used. Continuous or prolonged delivery may be achieved via an adhesive reservoir system.

Compounds or pharmaceutical compositions of the invention disclosed herein can be used in the manufacture of a medicament for treating, preventing, ameliorating or mitigating a neurological and psychiatric disorder or disease or a cancer in a subject, as well as other medicaments for modulating (e.g., blocking) dysfunctional glutamate transmission, and the compounds of this invention have superior pharmacokinetic and pharmacodynamic properties, fewer toxic side-effect.

Specifically, the amount of the compound of compositions of the present invention can effectively and detectably modulate dysfunctional glutamate transmission. The compounds or pharmaceutical compositions of the invention may be used for preventing, treating or alleviating diseases relating to dysfunctional glutamate transmission, wherein such diseases include glioma, breast cancer, melanoma; amyotrophic lateral sclerosis (ALS), chronic neuropathy pain, multiple sclerosis, ataxia, Parkinson's, Huntington's, Tourette syndrome, epilepsy, dystonia, Fragile X syndrome, disorders resulting from traumatic brain/spinal cord injuries, disorders resulting from cerebral ischemia; depression, anxiety, bipolar disorder, schizophrenia, obsessive compulsive disorder, autism, alcohol/drug addiction; vascular and Alzheimer's dementia, glaucoma induced optical neuropathy and attention deficit/hyperactive disorder (ADHD).

In one embodiment, the therapies disclosed herein comprise administrating a safe and effective amount of the compound of the invention or the pharmaceutical composition containing the compound of the invention to patients in need. Each example disclosed herein comprises the method of treating the diseases above comprising administrating a safe and effective amount of the compound of the invention or the pharmaceutical composition containing the compound of the invention to patients in need.

In one embodiment, the compound of the invention or the pharmaceutical composition thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, intravaginal, inhaled and intranasal administration. In one embodiment, the compound of the invention or the pharmaceutical composition thereof may be administered orally. In another embodiment, the compound of the invention or the pharmaceutical composition thereof may be administered by inhalation. In a further embodiment, the compound of the invention or the pharmaceutical composition thereof may be administered intranasal.

In one embodiment, the compound of the invention or the pharmaceutical composition thereof may be administered once or according to a dosing regimen wherein multiple doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as its absorption, distribution, and half-lives of metabolism and elimination, which can be determined by the skilled artisan. In addition, suitable dosing regimens, including the duration such regimens are administered, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's tolerance to the dosing regimen or over time as individual patient needs change.

The compounds of the present invention may be administered either simultaneously with, or before or after, one or more other therapeutic agents. The compounds of the present invention may be administered separately, by the same or different route of administration, or together in the same pharmaceutical composition as the other agents.

The pharmaceutical composition or combination of the present invention can be in unit dosage of about 1-1000 mg of active ingredients for a subject of about 50-70 kg, preferably about 1-500 mg or about 1-250 mg or about 1-150 mg or about 0.5-100 mg or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties can be correlated with in vitro and in vivo tests using advantageously mammals, e.g., mice, rats, dogs, non-human primates, such as monkeys or isolated organs, tissues and preparations thereof. The compounds of the present invention can be applied in vitro in the form of solutions, e.g., preferably aqueous solutions, and in vivo via topically, inhalingly, enterally or parenterally, advantageously intravenously, e.g., as a suspension or in aqueous solution.

In one embodiment, a therapeutically effective dosage of the compound disclosed herein from about 0.1 mg to about 1,000 mg per day. The pharmaceutical compositions should provide a dosage of from about 0.1 mg to about 1,000 mg of the compound. In a special embodiment, pharmaceutical dosage unit forms are prepared to provide from about 1 mg to about 1,000 mg, about 10 mg to about 500 mg, about 20 mg to about 200 mg, about 25 mg to about 100 mg, or about 30 mg to about 60 mg of the active ingredient or a combination of essential ingredients per dosage unit form. In a special embodiment, pharmaceutical dosage unit forms are prepared to provide about 1 mg, 5 mg, 10 mg, 20 mg, 25 mg, 50 mg, 100 mg, 250 mg, 500 mg, 1000 mg of the active ingredient.

ASPECTS OF THE INVENTION

The invention is further defined by the following aspects:

Aspect 1. A compound having Formula (A):

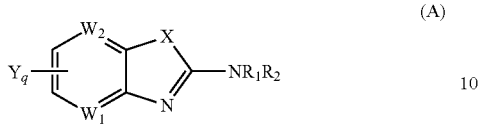

wherein,
- X is NH, O, S or Se;
- $W_1$ or $W_2$ is CH or N, provided that $W_1$ and $W_2$ are not both N;
- $R_1$ and $R_2$ are the same, or they are different, and are independently selected from the group consisting of:
  - Hydrogen and
  - $GR^a$, wherein G is absent, —C(O)— or —C(O)O— and $R^a$ is a saturated straight or branched alkyl of from one to four carbon atoms, or a saturated cycloalkyl of from three to six carbon atoms, provided that $R_1$ and $R_2$ are not both $GR^a$, wherein G is not absent;
- $Y_q$ is selected from the group consisting of hydrogen, deuterium, $SF_5$, $CF_3$, $OCF_3$, $SCF_3$, $S(O)CF_3$, $S(O)_2CF_3$, CN, SCN, $S(O)CH_3$, $S(O)_2CH_3$, $NO_2$, and wherein q is 1 or 2; provided that when q is 2, $Y_1$ and $Y_2$ can be the same, or different, and they are not both hydrogen, or both deuterium, or one each of hydrogen and deuterium;

or a pharmaceutically acceptable salt thereof, and with the proviso that when $W_1$ and $W_2$ are CH, the compound of Formula (A) is not one of the following compounds:

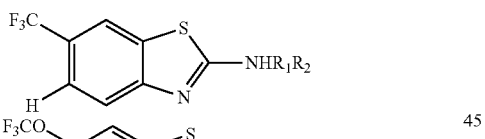

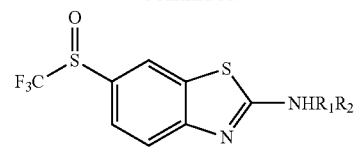

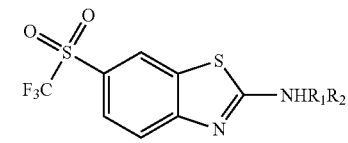

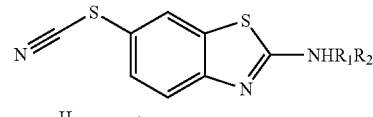

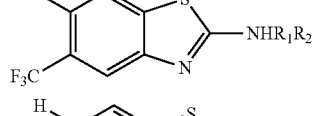

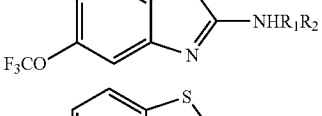

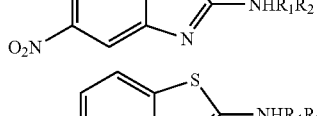

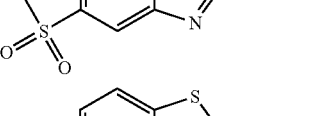

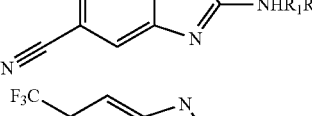

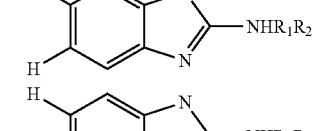

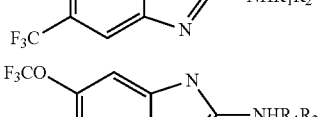

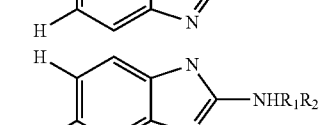

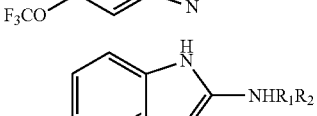

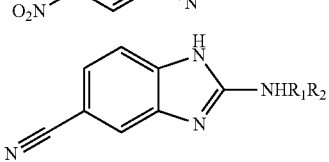

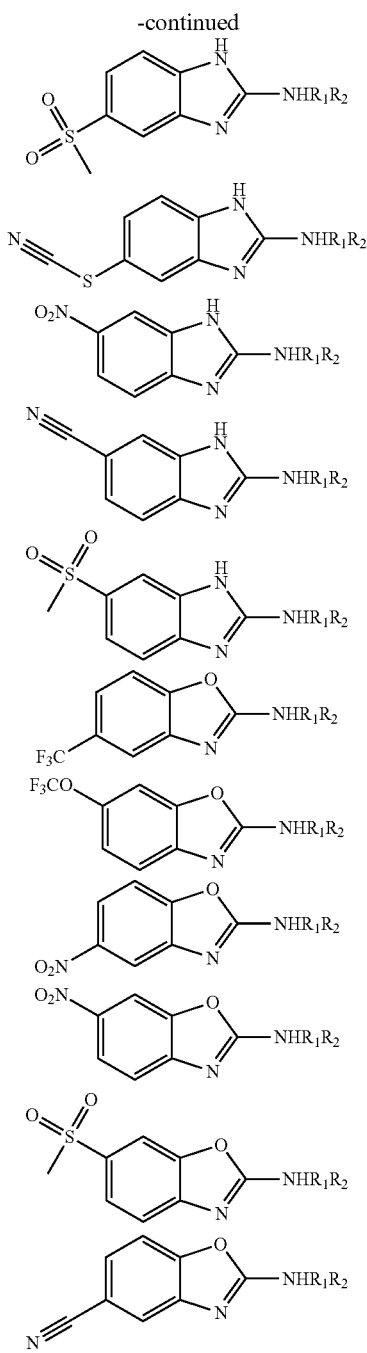

wherein R₁ or R₂ are as above defined; and with the proviso that when W₁ or W₂ is N, the compound of Formula (A) is not one of the following compounds:

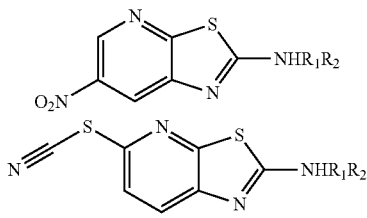

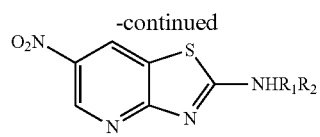

wherein R₁ or R₂ are as above defined.

Aspect 2. The compound of aspect 1, wherein X is NH.
Aspect 3. The compound of aspect 1, wherein X is O.
Aspect 4. The compound of aspect 1, wherein X is S.
Aspect 5. The compound of aspect 1, wherein X is Se.
Aspect 6. The compound of any one of aspects 1 to 5, wherein W₁ and W₂ are CH.
Aspect 7. The compound of Claim 1, wherein W₁ or W₂ is N, provided that W₁ and W₂ are not both N.
Aspect 8. The compound of any one of aspects 1 to 5, wherein Y₁ or Y₂ is hydrogen or deuterium, provided that Y₁ and Y₂ are not: both hydrogen, or both deuterium, or one each of hydrogen and deuterium.
Aspect 9. The compound of any one of aspects 1 to 8, wherein $Y_q$ is SF₅ and q is 1 or 2.
Aspect 10. The compound of any one of aspects 1 to 8, wherein $Y_q$ is CF₃ and q is 1 or 2.
Aspect 11. The compound of any one of aspects 1 to 8, wherein $Y_q$ is OCF₃ and q is 1 or 2.
Aspect 12. The compound of any one of aspects 1 to 8, wherein $Y^q$ is SCF₃ and q is 1 or 2.
Aspect 13. The compound of any one of aspects 1 to 8, wherein $Y_q$ is S(O)CF₃ and q is 1 or 2.
Aspect 14. The compound of any one of aspects 1 to 8, wherein $Y_q$ is S(O)₂CF₃ and q is 1 or 2.
Aspect 15. The compound of any one of aspects 1 to 8, wherein Yq is CN and q is 1 or 2.
Aspect 16. The compound of any one of aspects 1 to 8, wherein $Y_q$ is SCN and q is 1 or 2.
Aspect 17. The compound of any one of aspects 1 to 8, wherein $Y_q$ is S(O)CH₃ and q is 1 or 2.
Aspect 18. The compound of any one of aspects 1 to 8, wherein $Y_q$ is S(O)₂CH₃ and q is 1 or 2.
Aspect 19. The compound of any one of aspects 1 to 8, wherein $Y_q$ is NO₂ and q is 1 or 2.
Aspect 20. The compound of any one of aspects 1 to 19, wherein R₁ or R₂ is hydrogen.
Aspect 21. The compound of any one of aspects 1 to 19, wherein R₁ or R₂ is GR$^a$, wherein G is absent and R$^a$ is a straight or branched alkyl of from one to four carbon atoms, and is selected from the group consisting of: —CH₃, —CH₂CH₃, —CH₂CH₂CH₃, —CH(CH₃)₂, —CH₂CH₂CH₂CH₃, —CH₂CH(CH₃)₂, and —C(CH₃)₃.
Aspect 22. The compound of any one of aspects 1 to 19, wherein R₁ or R₂ is GR$^a$, wherein G is absent and R$^a$ is a cycloalkyl of from three to six carbon atoms, and is selected from the group consisting of:

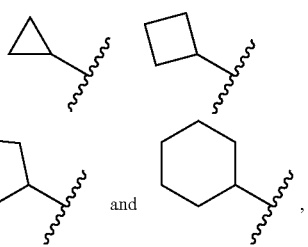

optionally, R$^a$ is substituted with C₁-C₄ alkyl.

Aspect 23. The compound of any one of aspects 1 to 19, wherein one of $R_1$ and $R_2$ is $GR^a$, wherein G is —C(O)— and $R^a$ is a saturated straight or branched alkyl of from one to four carbon atoms, or a saturated cycloalkyl of from three to six carbon atoms, and is selected from the group consisting of:

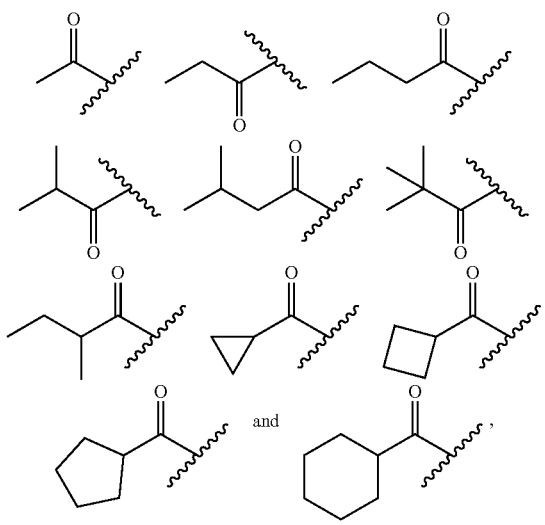

optionally, $R^a$ is substituted with $C_1$-$C_4$ alkyl.

Aspect 24. The compound of any one of aspects 1 to 19, wherein one of $R_1$ and $R_2$ is $GR^a$, wherein G is —C(O)O— and $R^a$ is a saturated straight or branched alkyl having from one to four carbon atoms, or a saturated cyclic alkyl having from three to six carbon atoms, and is selected from the group consisting of:

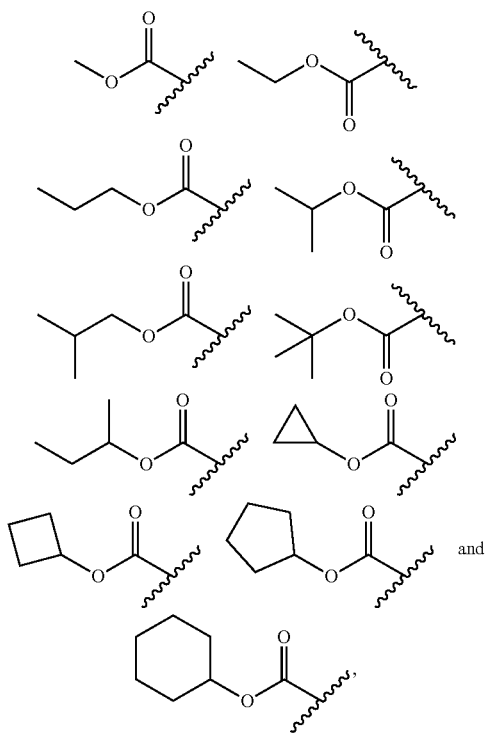

optionally, $R^a$ is optionally substituted with $C_1$-$C_4$ alkyl.

Aspect 25. The compound of any one of aspects 1 to 24, wherein $R^a$ is selected from the group consisting of a saturated straight or branched alkyl of from one to four carbon atoms, and a saturated cycloalkyl of from three to six carbon atoms, wherein one or more of said carbon atoms is, optionally, an asymmetric atom.

Aspect 26. The compound of aspect 1, wherein $W_1$ and $W_2$ are CH, X is N, $Y_1$ is $SF_5$, $Y_2$ is H or D.

Aspect 27. The compound of aspect 1, wherein $W_1$ and $W_2$ are CH, X is N, $Y_1$ and $Y_2$ are $SF_5$.

Aspect 28. The compound of aspect 1, wherein $W_1$ and $W_2$ are CH, X is O, $Y_1$ is $SF_5$, $Y_2$ is H or D.

Aspect 29. The compound of aspect 1, wherein $W_1$ and $W_2$ are CH, X is O, $Y_1$ and $Y_2$ are $SF_5$.

Aspect 30. The compound of aspect 1, wherein $W_1$ and $W_2$ are CH, X is S, $Y_1$ is $SF_5$, $Y_2$ is H or D.

Aspect 31. The compound of aspect 1, wherein $W_1$ and $W_2$ are CH, X is S, $Y_1$ and $Y_2$ are $SF_5$.

Aspect 32. The compound of aspect 1, wherein $W_1$ and $W_2$ are CH, X is Se, $Y_1$ is $SF_5$, $Y_2$ is H or D.

Aspect 33. The compound of aspect 1, wherein $W_1$ and $W_2$ are CH, X is Se, $Y_1$ and $Y_2$ are $SF_5$.

Aspect 34. The compound of aspect 1, wherein $W_1$ and $W_2$ are CH, X is Se, $Y_1$ is selected from the group consisting of $CF_3$, $OCF_3$, $SCF_3$, $S(O)CF_3$, $S(O)_2CF_3$, CN, SCN, $S(O)CH_3$, $S(O)_2CH_3$, and $NO_2$, $Y_2$ is H or D.

Aspect 35. The compound of aspect 1, wherein $W_1$ or $W_2$ is N, X is N or O or S or Se, $Y_1$ is $SF_5$, $Y_2$ is H or D.

Aspect 36. The compound of aspect 1, wherein $W_1$ or $W_2$ is N, X is N or O or S or Se, $Y_1$ is $CF_3$, $Y_2$ is H or D.

Aspect 37. The compound of aspect 1, wherein $W_1$ or $W_2$ is N, X is N or O or S or Se, $Y_1$ is $OCF_3$, $Y_2$ is H or D.

Aspect 38. The compound of aspect 1, wherein $W_1$ or $W_2$ is N, X is N or O or S or Se, $Y_1$ is selected from the group consisting of $SCF_3$, $S(O)CF_3$, $S(O)_2CF_3$, CN, SCN, $S(O)CH_3$, $S(O)_2CH_3$, and $NO_2$, $Y_2$ is H or D.

Aspect 39. A compound selected from the group consisting of

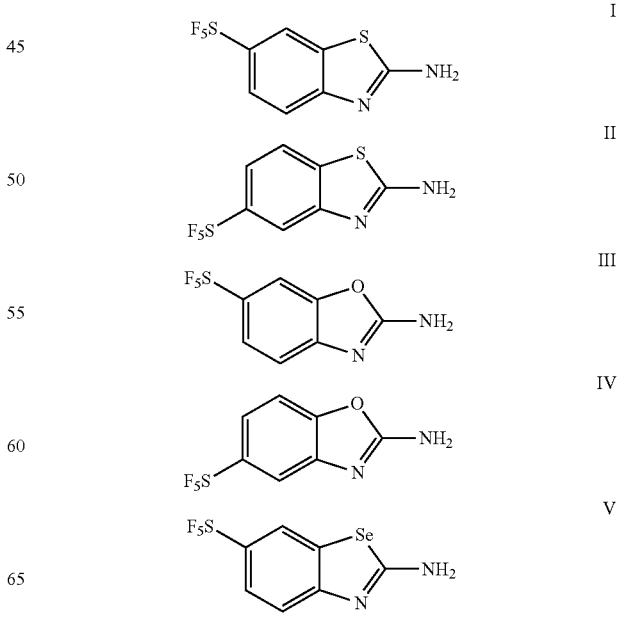

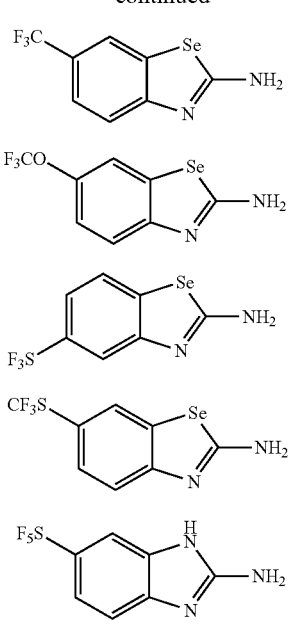

and pharmaceutically acceptable salts thereof.

Aspect 40. A pharmaceutical composition comprising a therapeutically effective amount of at least one compound according to any one of aspects 1 to 39, or a pharmaceutically acceptable salt thereof.

Aspect 41. The pharmaceutical composition of aspect 40, further comprising a pharmaceutically acceptable excipient, carrier, adjuvant, solvent, support or a combination thereof.

Aspect 42. The pharmaceutical composition of aspect 40, further comprising therapeutically effective amounts of one or more, optional, adjunctive active ingredients.

Aspect 43. The pharmaceutical composition of aspect 42, wherein the adjunctive active ingredient is for preventing or treating a neurological and psychiatric disorder or disease, and comprises an antipsychotic, an atypical antipsychotic, an antiepileptic, an anti-Parkinson's disease drug, an anti-amyotrophic lateral sclerosis drug, anti-pain drug, anti-multiple sclerosis drug, spinal cord injury or a combination thereof.

Aspect 44. The pharmaceutical composition of aspect 43, wherein the active ingredient comprises riluzole, amitriptyline, desipramine, mirtazapine, bupropion, reboxetine, fluoxetine, trazodone, sertraline, duloxetine, fluvoxamine, milnacipran, levomilnacipran, desvenlafaxine, vilazodone, venlafaxine, dapoxetine, nefazodone, femoxetine, clomipramine, citalopram, escitalopram, paroxetine, lithium carbonate, buspirone, olanzapine, quetiapine, risperidone, ziprasidone, aripiprazole, perospirone, clozapine, modafinil, mecamylamine, cabergoline, adamantane, imipramine, pramipexole, thyroxine, dextromethorphan, quinidine, naltrexone, samidorphan, buprenorphine, melatonin, alprazolam, pipamperone, vestipitant, perphenazine, midazolam, triazolam, estazolam, diazepam, flurazepam, nitrazepam, clonazepam, temazepam, flunitrazepam, oxazepam, zolpidem, zaleplon, zopiclone, eszopiclone, indiplon, tiagabine, gaboxadol, clomipramine, doxepin, chloral hydrate, haloperidol, chlorpromazine, carbamazepine, promethazine, lorazepam, hydroxyzine, aspirin, diphenhydramine, chlorpheniramine, lendormin, ramelteon, tasimelteon, agomelatine, mianserin, femoxetine, nabilone, doxepin, gabapentin, chlordiazepoxide, suvorexant, Xuezang Guben or a combination thereof.

Aspect 45. The pharmaceutical composition of aspect 42, wherein the adjunctive active ingredient is for preventing or treating a cancer, and comprises a chemotherapeutic agent.

Aspect 46. The pharmaceutical composition of aspect 45, wherein said adjunctive active agent, or chemotherapeutic agent is selected from the group consisting of: cytotoxic agent, cisplatin, doxorubicin, taxotere, taxol, etoposide, irinotecan, camptostar, topotecan, paclitaxel, docetaxel, the epothilones, tamoxifen, 5-fluorouracil, methoxtrexate, temozolomide, cyclophosphamide, SCH 66336, tipifarnib, R115777, L778,123, BMS 214662, Iressa®, Tarceva®, C225, GLEEVEC®, Intron®, Peg-Intron®, aromatase combinations, ara-C, adriamycin, ercept, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin, Pentostatine, Vinblastine, Vincristine, Vindesine, Bleomycin, Dactinomycin, Daunorubicin, Epirubicin, Idarubicin, Mithramycin™, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrol acetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Fulvestrant, Exemestane, Ifosfomide, Rituximab, Campath, leucovorin, and dexamethasone, bicalutamide, carboplatin, chlorambucil, letrozole, megestrol, and valrubicin.

Aspect 47. Use of the compound according to any one of aspects 1 to 40 or the pharmaceutical composition according to any one of claims 40 to 46 in the manufacture of a medicament for preventing, treating or lessening a disorder or disease in a patient by modulating glutamate transmission in said patient.

Aspect 48. The use of the compound or pharmaceutical composition according to aspect 47, wherein the disorder or disease is a neurological and psychiatric disorder or disease or a disorder or disease affecting the central nervous system.

Aspect 49. The use of the compound or pharmaceutical composition according to aspect 48, wherein the neurological and psychiatric disorder or disease, or the disorder or disease affecting the CNS, is selected from the group consisting of amyotrophic lateral sclerosis, chronic neuropathy pain, multiple sclerosis, ataxia, Parkinson's, Huntington's, Tourette syndrome, epilepsy, dystonia, Fragile X syndrome, disorders resulting from traumatic brain/spinal cord injuries, disorders resulting from cerebral ischemia; depression, anxiety, bipolar disorder, schizophrenia, obsessive compulsive disorder, autism, alcohol/drug addiction; vascular and Alzheimer's dementia, glaucoma induced optical neuropathy and attention deficit/hyperactive disorder.

Aspect 50. The use of the compound or pharmaceutical composition according to aspect 47, wherein the disorder or disease is a cancer.

Aspect 51. The use of the compound or pharmaceutical composition according to aspect 50, wherein the cancer is selected from the group consisting of glioma, breast cancer and melanoma.

Aspect 52. The compound according to any one of aspects 1 to 39 or the pharmaceutical composition according to any one of aspects 40 to 46 for use in preventing, treating or lessening a disorder or disease in a human patient by modulating glutamate transmission in said patient.

Aspect 53. The compound or pharmaceutical composition for use according to aspect 52, wherein the disorder or disease is a neurological and psychiatric disorder or disease or a disorder or disease affecting the central nervous system.

Aspect 54. The compound or pharmaceutical composition for use according to aspect 53, wherein the neurological and psychiatric disorder or disease, or the disorder or disease affecting the CNS, is selected from the group consisting of amyotrophic lateral sclerosis, chronic neuropathy pain, multiple sclerosis, ataxia, Parkinson's, Huntington's, Tourette syndrome, epilepsy, dystonia, Fragile X syndrome, disorders resulting from traumatic brain/spinal cord injuries, disorders resulting from cerebral ischemia; depression, anxiety, bipolar disorder, schizophrenia, obsessive compulsive disorder, autism, alcohol/drug addiction; vascular and Alzheimer's dementia, glaucoma induced optical neuropathy and attention deficit/hyperactive disorder.

Aspect 55. The compound or pharmaceutical composition for use according to aspect 52, wherein the disorder or disease is a cancer.

Aspect 56. The compound or pharmaceutical composition for use according to aspect 55, wherein the cancer is selected from the group consisting of glioma, breast cancer and melanoma.

Aspect 57. A method for preventing, treating or lessening a disorder or disease in a patient by modulating glutamate transmission in said patient comprising administering to the patient a therapeutically effective amount of a compound according to any one of aspects 1 to 39 or a pharmaceutical composition according to any one of aspects 40 to 46.

Aspect 58. The method of aspect 57, wherein the disorder or disease is a neurological and psychiatric disorder or disease or a disorder or disease affecting the central nervous system.

Aspect 59. The method of aspect 58, wherein the neurological and psychiatric disorder or disease, or the disorder or disease affecting the CNS, is selected from the group consisting of amyotrophic lateral sclerosis, chronic neuropathy pain, multiple sclerosis, ataxia, Parkinson's, Huntington's, Tourette syndrome, epilepsy, dystonia, Fragile X syndrome, disorders resulting from traumatic brain/spinal cord injuries, disorders resulting from cerebral ischemia; depression, anxiety, bipolar disorder, schizophrenia, obsessive compulsive disorder, autism, alcohol/drug addiction; vascular and Alzheimer's dementia, glaucoma induced optical neuropathy and attention deficit/hyperactive disorder.

Aspect 60. The method of aspect 57, wherein the disorder or disease is a cancer.

Aspect 61. The method of aspect 60, wherein the cancer is selected from the group consisting of glioma, breast cancer and melanoma.

EXAMPLES

The following examples are provided so that the invention might be more fully understood. However, it should be understood that these embodiments merely provide a method of practicing the present invention, and the present invention is not limited to these embodiments.

Generally, the compounds disclosed herein may be prepared by methods described herein, wherein the substituents are as defined for Formula (A) above, except where further noted. The following non-limiting schemes and examples are presented to further exemplify the invention.

Professionals skilled in the art will recognize that the chemical reactions described may be readily adapted to prepare a number of other compounds disclosed herein, and alternative methods for preparing the compounds disclosed herein are deemed to be within the scope disclosed herein. Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, such need for protecting groups, as well as the conditions necessary to attach and remove such groups, will be apparent to those skilled in the art of organic synthesis. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, the known reaction conditions or the reaction disclosed in the present invention will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated.

Preparation of Compounds

Compounds of the present invention, including salts, esters, hydrates, or solvates thereof, can be prepared using any known organic synthesis techniques and can be synthesized according to any of numerous possible synthetic routes.

The reactions for preparing compounds of the present invention can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety) and normal phase silica chromatography.

Compounds of the present invention can be synthesized using the methods described below, together with synthetic methods known in the art of synthetic organic chemistry, or variations thereon as appreciated by those skilled in the art. Preferred methods include but are not limited to those methods described below. Specifically, the compounds of the present invention of Formula (A) can be synthesized by following the steps outlined in the exemplary general synthetic schemes listed below, and the abbreviations for the reactants or for the chemical groups of the reactants included in the synthetic schemes are defined in the Examples.

General Synthetic Schemes (1-13)

Scheme 1
General synthesis of $Y_q$-substituted-benzol[d]thiazol-2-amine (XI)

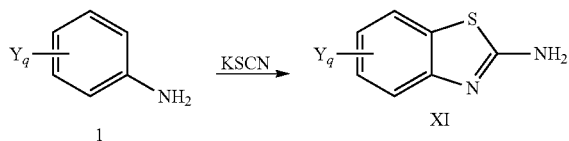

The synthesis towards compounds having formula XI can be conducted according to the relevant procedures disclosed in references (*Synlett*, 2012, 23, 15, 2219-2222; PCT International Publication No. WO 2013/163244 A1), but is not limited to these disclosed procedures. Thus, an aniline derivative 1 is treated with KSCN in appropriate solvent system to form Compound XI.

Scheme 2
General synthesis of $Y_q$-substituted-benzol[d]oxazol-2-amine (XII)

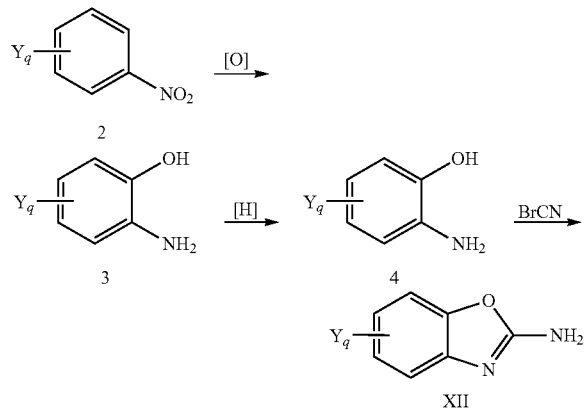

The synthesis towards compounds having formula XII can be conducted according to the relevant procedures disclosed in references (*Journal of Organic Chemistry*, 1990, 55, 17, 4979-4981; *Tetrahedron Letters*, 2011, 52, 34, 4392-4394; and *Bioorganic and Medicinal Chemistry Letters*, 2014, 24, 15, 3521-3525), but is not limited to these disclosed procedures. Thus, a nitrobenzene derivative 2 is oxidized to generate hydroxyl compound 3, followed by hydrogenation, the resulting amino compound 4 is treated with BrCN in appropriate solvent system to form Compound XII.

Scheme 3
General synthesis of $Y_q$-substituted 1H-benzo[d]imidazol-2-amine (XIII)

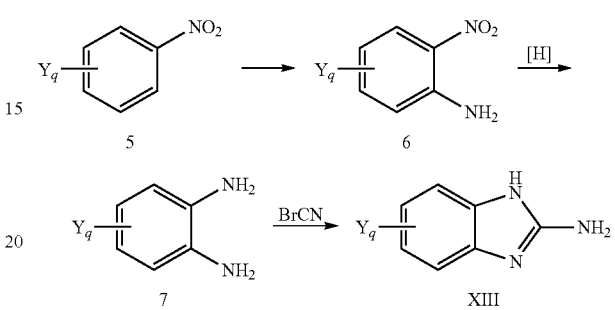

The synthesis towards compounds having formula XIII can be conducted according to the relevant procedures disclosed in references (*European Journal of Organic Chemistry*, 2012, 11, 2123-2126; *Journal of Medicinal Chemistry*, 2014, 57, 17, 7325-7341; U.S. Application Publication No. 2007/117818 A1), but is not limited to these disclosed procedures. Thus, a nitrobenzene derivative 5 is transformed to compound 6, followed by hydrogenation, the resulting diamino compound 7 is treated with BrCN in appropriate solvent system to form Compound XIII.

Scheme 4
General synthesis of $Y_q$-substituted benzo[d][1,3]selenazol-2-amine (XIV)

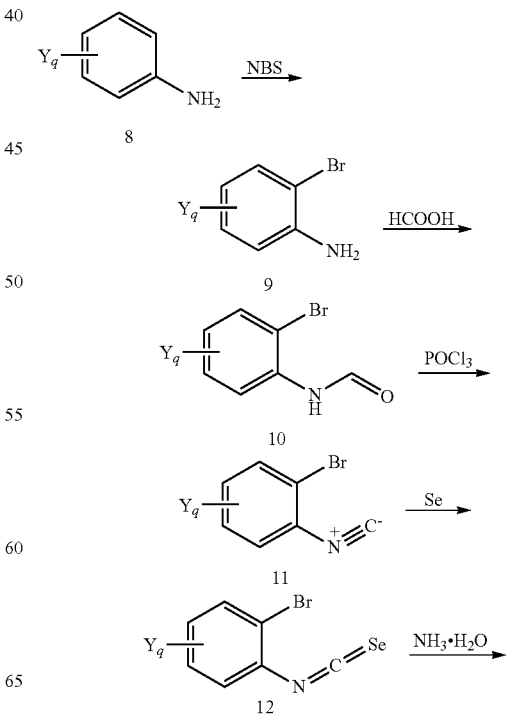

-continued

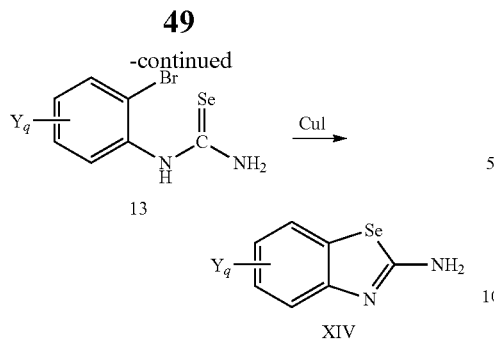

The synthesis towards compounds having formula XIV can be conducted according to the relevant procedures disclosed in references (*European Journal of Medicinal Chemistry*, 2015, 96, 92-97; Synthesis, 2016, 48, 01, 85-96; and *European Journal of Organic Chemistry*, 2011, 25, 4756-4759), but is not limited to these disclosed procedures. Thus, an aniline derivative 8 is brominated to furnish compound 9, which is further converted to amide compound 10. Compound 10 is treated with POCl$_3$ to generate compound 11, followed by successive treatment of Se and NH$_4$OH, the resulting compound 13 is cyclized in appropriate solvent system to form Compound XIV.

Scheme 5
General synthesis of $Y_q$-subtituted thiazolo[5,4-b]pyridin-2-amine (XV)

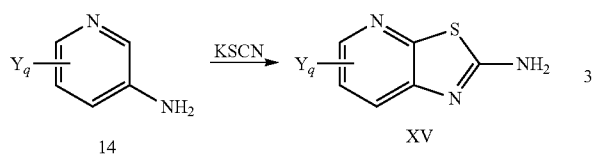

The synthesis towards compounds having formula XV can be conducted according to the relevant procedures disclosed in references (*Journal of Medicinal Chemistry*, 2009, 52, 19, 6142-6152; U.S. Application Publication No. 2009/270405 A1), but is not limited to these disclosed procedures. Thus, an amino pyridine derivative 14 is treated with KSCN in appropriate solvent system to form Compound XV.

Scheme 6
General synthesis of $Y_g$-substituted oxazolo[5,4-b]pyridin-2-amine (XVI)

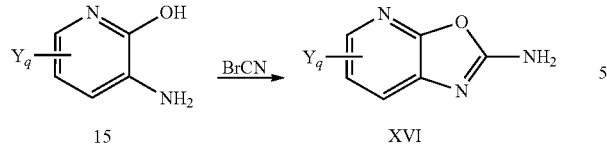

The synthesis towards compounds having formula XVI can be conducted according to the relevant procedures disclosed in references (PCT International Publication No. WO 2013/177024 A1; and PCT International Publication No. WO 2009/147431 A1), but is not limited to these disclosed procedures. Thus, a pyridine derivative 15 is treated with BrCN in appropriate solvent system to form Compound XVI.

Scheme 7
General synthesis of $Y_g$-substituted 3H-imidazo[5,4-b]pyridin-2-amine (XVI)

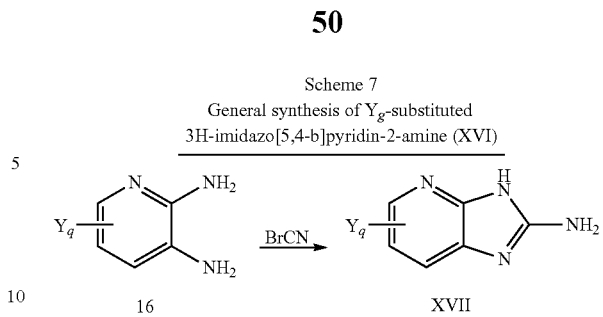

The synthesis towards compounds having formula XVII can be conducted according to the relevant procedures disclosed in references (*Chemical Communications*, 2014, 50, 85, 12911-12914; *Journal of Medicinal Chemistry*, 2014, 57, 13, 5702-5713), but is not limited to these disclosed procedures. Thus, a diamino pyridine derivative 16 is treated with BrCN in appropriate solvent system to form Compound XVII.

Scheme 8
General synthesis of $Y_q$-substituted[1,3]selenazolo[5,4-b]pyridin-2-amine (XVIII)

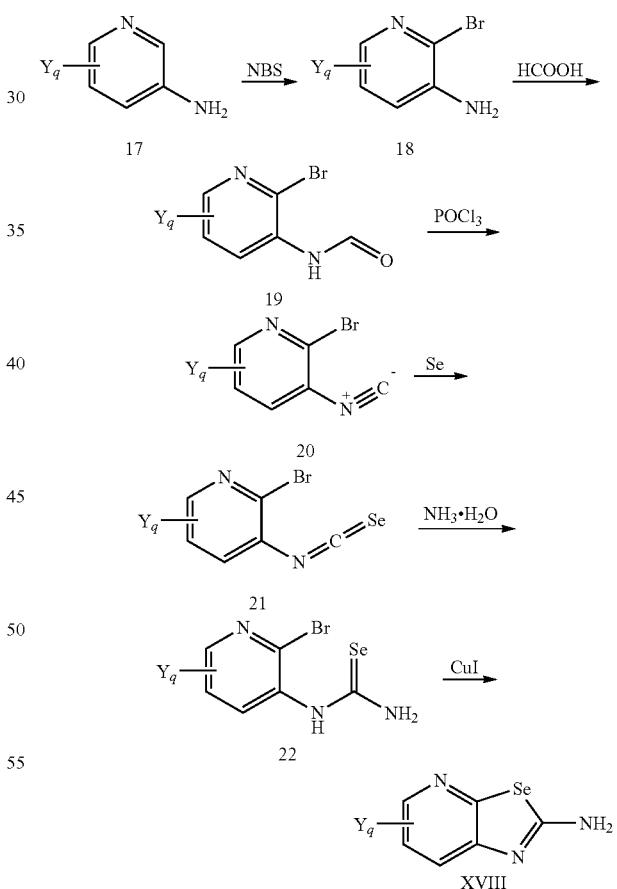

The synthesis towards compounds having formula XVIII can be conducted according to the relevant procedures disclosed in references (U.S. Application Publication No. 2003/171395 A1; *Synthesis*, 2001, 14, 2175-2179; Synthesis, 2016, 48, 01, 85-96; and *European Journal of Organic Chemistry*, 2011, 25, 4756-4759), but is not limited to these disclosed procedures. Thus, an amino pyridine derivative 17 is brominated to furnish compound 18, which is further converted to amide compound 19. Compound 19 is treated with POCl₃ to generate compound 20, followed by successive treatment of Se and NH₄OH, the resulting compound 22 is cyclized in appropriate solvent system to form Compound Scheme 9

Scheme 9
General synthesis of Y$_g$-substituted thiazolo[4,5-b]pyridin-2-amine (XIX)

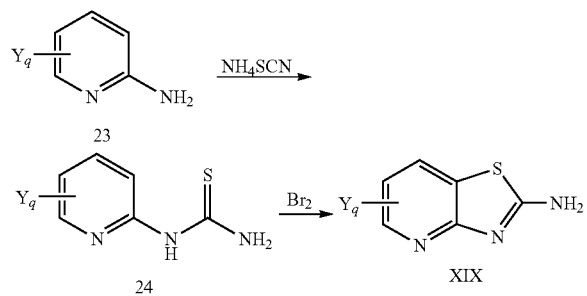

The synthesis towards compounds having formula XIX can be conducted according to the relevant procedures disclosed in references (*Journal of Heterocyclic Chemistry*, 2003, 40, 2, 261-268; *Phosphorus, Sulfur and Silicon and the Related Elements*, 2006, 181, 7, 1665-1673), but is not limited to these disclosed procedures. Thus, an amino pyridine derivative 23 is treated with NH₄SCN to generate compound 24, which is further cyclized in appropriate solvent system to form Compound XIX.

Scheme 10
General synthesis of Y$_g$-substituted oxazolo[4,5-b]pyridin-2-amine (XX)

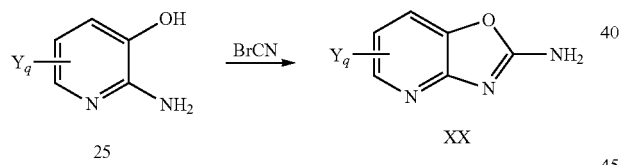

The synthesis towards compounds having formula XX can be conducted according to the relevant procedures disclosed in references (U.S. Application Publication No. 2012/149718 A1; German Application Publication No. DE2239311), but is not limited to these disclosed procedures. Thus, a pyridine derivative 25 is treated with BrCN in appropriate solvent system to form Compound XX.

Scheme 11
General synthesis of Y$_g$-substituted 1H-imidazol[4,5-b]pyridin-2-amine (XXI)

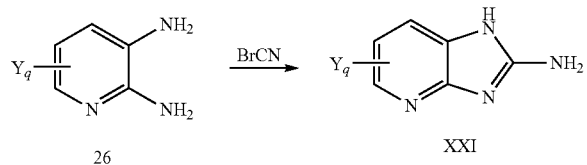

The synthesis towards compounds having formula XXI can be conducted according to the relevant procedures disclosed in references (*Journal of Heterocyclic Chemistry*, 1990, 27, 6, 1821-1824; *Chemical Communications*, 2014, 50, 85, 12911-12914), but is not limited to these disclosed procedures. Thus, a diamino pyridine derivative 26 is treated with BrCN in appropriate solvent system to form Compound XXI.

Scheme 12
General synthesis of Y$_g$-substituted [1,3]selenazolo[4,5-b]pyridin-2-amine (XXII)

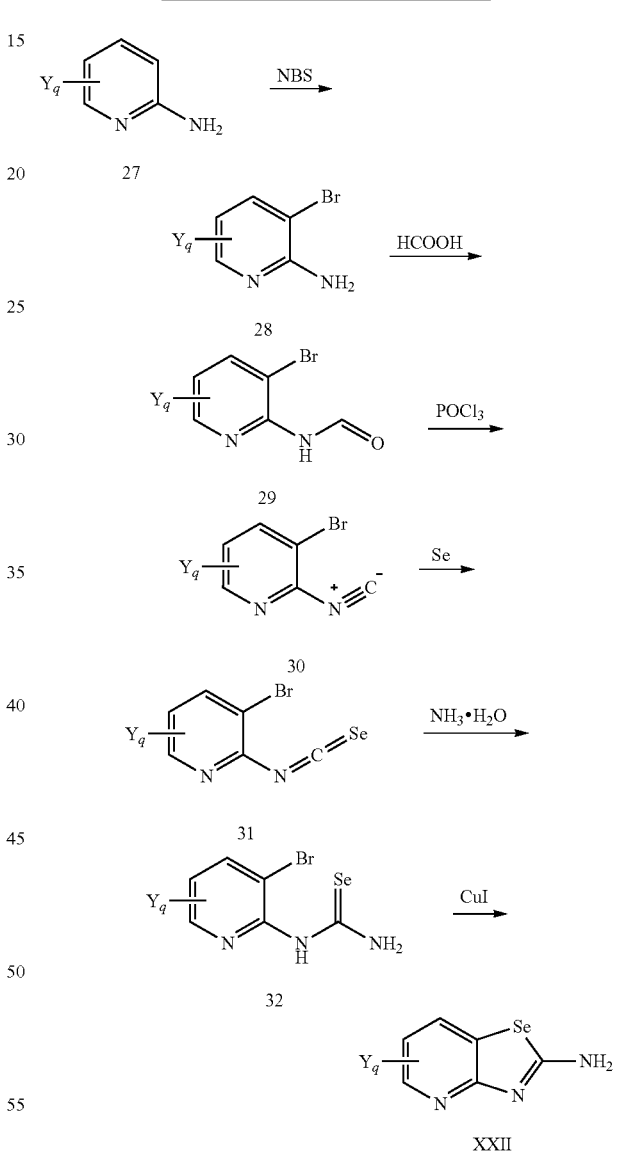

The synthesis towards compounds having formula XXII can be conducted according to the relevant procedures disclosed in references (*Organic Letters*, 2016, 18, 5, 984-987; *European Journal of Medicinal Chemistry*, 2015, 96, 92-97; and *European Journal of Organic Chemistry*, 2011, 25, 4756-4759), but is not limited to these disclosed procedures. Thus, an amino pyridine derivative 27 is brominated to furnish compound 28, which is further converted to amide compound 29. Compound 29 is treated with POCl₃ to generate compound 30, followed by successive treatment of Se and NH₄OH, the resulting compound 32 is cyclized in appropriate solvent system to form Compound XXII.

Scheme 13
General synthesis of $Y_g$-substituted amine derivate having formula A

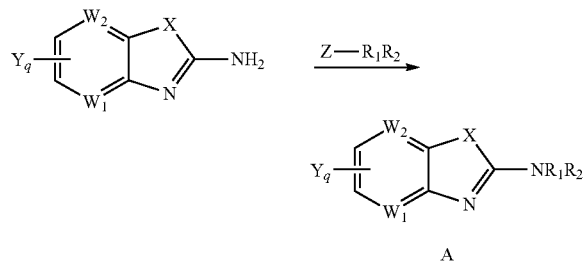

A

The synthesis towards compounds having formula A can be conducted starting from amino compounds having formula I-XXII according to the relevant procedures disclosed in references, but is not limited to these disclosed procedures.

Wherein, $R_1$ and $R_2$ are not both H, Z is a leaving group that can be selected from Cl, Br, or I. The amino compounds I-XXII can be converted to corresponding N-acyl or N-acyloxy compounds via typical N-acylation procedures (*Journal of Medicinal Chemistry*, 2012, 55, 11, 5554-5565; U.S. Application Publication No. 2015/225407 A1, *Bioorganic and Medicinal Chemistry*, 2012, 20, 18, 5642-5648; and PCT International Publication No. WO 2010/100144 A1).

Wherein, $R_1$ and $R_2$ are not both H. The amino compounds I-XXII can be converted to corresponding N-alkyl compounds via a variety of methods (*Synlett*, 2013, 24, 17, 2249-2254; *Chemical Communications*, 2012, 48, 4, 603-605; *Journal of Medicinal Chemistry*, 1999, 42, 15, 2828-2843; *European Journal of Medicinal Chemistry*, 2014, 74, 703-716; *Angewandte Chemie—International Edition*, 2015, 54, 31, 9042-9046; and U.S. Application Publication No. 2004/44258 A1).

Preparation and Characterization of Exemplary Compounds

Compounds encompassed in the present disclosure may be prepared via different schemes. Detailed preparation processes of 10 exemplary compounds via various schemes are described below and the characterization results are listed as well.

Unless stated otherwise, all reagents were purchased from commercial suppliers without further purification. Solvent drying by standard methods was employed when necessary. The plates used for thin-layer chromatography (TLC) were E. Merck silica gel 60F254 (0.24 nm thickness) precoated on aluminum plates, and then visualized under UV light (365 nm and 254 nm) or through staining with a 5% of dodecamolybdophosphoric acid in ethanol and subsequent heating. Column chromatography was performed using silica gel (200-400 mesh) from commercial suppliers. ¹H-NMR spectra were recorded on an Agilent 400-MR NMR spectrometer (400.00 MHz for 1H) at room temperature. Solvent signal was used as reference for ¹H-NMR (CDCl₃, 7.26 ppm; CD₃OD, 3.31 ppm; DMSO-d6, 2.50 ppm; D₂O, 4.79 ppm). The following abbreviations were used to explain the multiplicities: s=singlet, d=doublet, t=triplet, q=quartet, br. s.=broad singlet, dd=double doublet, td=triple doublet, dt=double triplet, dq=double quartet, m=multiplet. Other abbreviations used in the experimental details are as follows: δ=chemical shift in parts per million downfield from tetramethylsilane, Ar=aryl, Ac=acyl, Boc=tert-butyloxy carbonyl, Bn=Benzyl, DCM=dichloromethane, DMF=N,N'-dimethylformamide, DIPEA=diisopropylethylamine, DMAP=4-(dimethylamino)pyridine, DMSO=dimethyl sulphoxide, EA=ethyl acetate, Et=ethyl, Me=methyl, Hz=hertz, HPLC=high performance liquid chromatography, J=coupling constant (in NMR), min=minute(s), h=hour(s), NMR=nuclear magnetic resonance, prep=preparative, t-Bu=tert-butyl, iPr=isopropyl, TBAF=tetrabutylammonium fluoride, tert=tertiary, TFA=trifluoroacetic acid, THF=tetrahydrofuran, TLC=thin-layer chromatography.

EXAMPLES

It should be noted that embodiments of the present invention described in detail below are exemplary for explaining the present invention only, and not be construed as limiting the present invention. Examples without a specific technology or condition can be implemented according to technology or condition in the documentation of the art or according to the product instructions. The reagents or instruments without manufacturers are available through conventional purchase. Those having skill in the art will recognize that the starting materials may be varied and additional steps employed to produce compounds encompassed by the present inventions, as demonstrated by the following examples.

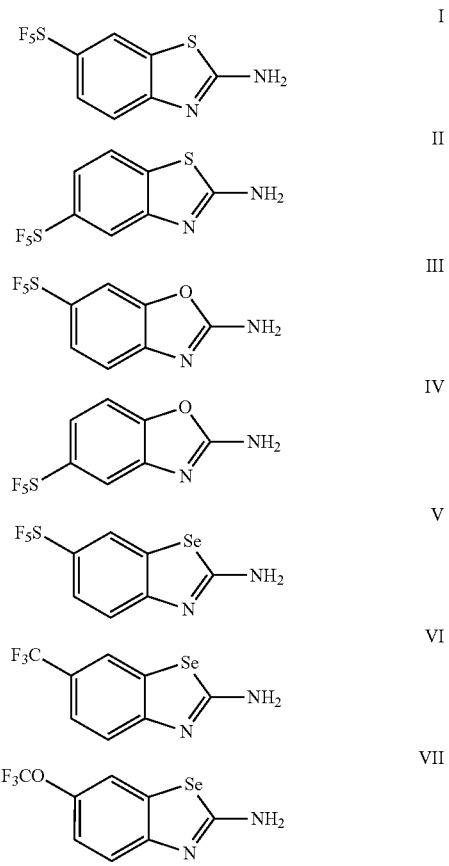

-continued

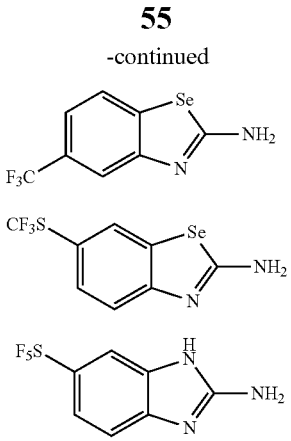

Example 1

6-(Pentafluorosulfanyl)benzo[d]thiazol-2-amine (I)

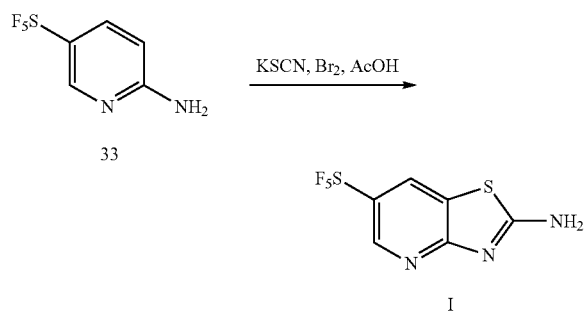

To a stirred solution of 4-(pentafluorosulfanyl)aniline (33) (500 mg, 2.28 mmol) in AcOH (10 mL) was added KSCN (265 mg, 2.73 mmol) in one portion at 20° C. After stirring for 30 min, the reaction mixture was cooled to 0° C. and a solution of Br$_2$ (365 mg, 2.28 mmol) in AcOH (1 mL) was added dropwise. Then the ice-bath was removed, the reaction mixture was stirred at 20° C. for 16 h. The mixture was poured into water (100 mL), and extracted with CH$_2$Cl$_2$ (3×30 mL). The combined organic phase was washed with water saturated NaHCO$_3$ solution (15 mL), saturated brine water solution (15 mL), dried over anhydrous Na$_2$SO$_4$ and evaporated. The residue was purified by prep-HPLC to afford the titled compound I (378 mg, 60%) as a white solid. $^1$H-NMR (400 MHz, DMSO-d$_6$) δ=8.34 (d, J=2.0 Hz, 1H), 7.97 (s, 2H), 7.68 (dd, J=2.2 Hz, 9.0 Hz, 1H), 7.40 (d, J=9.2 Hz, 1H); MS (ESI): [M+H$^+$]=276.9.

Example 2

5-(Pentafluorosulfanyl)benzo[d]thiazol-2-amine (II)

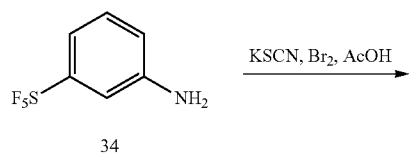

-continued

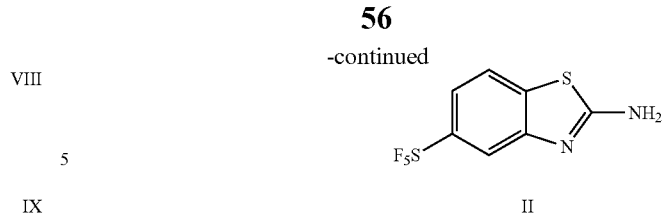

To a stirred solution of 3-(pentafluorosulfanyl)aniline (34) (400 mg, 1.83 mmol) in AcOH (8 mL) was added KSCN (355 mg, 3.65 mmol) in one portion at 20° C. After stirring for 30 min, the reaction mixture was cooled to 0° C. and a solution of Br$_2$ (292 mg, 1.83 mmol) in AcOH (1 mL) was added dropwise. Then the ice-bath was removed, the reaction mixture was stirred at 20° C. for 16 h. The mixture was poured into water (100 mL), and extracted with CH$_2$Cl$_2$ (3×30 mL). The combined organic phase was washed with saturated NaHCO$_3$ water solution (15 mL), saturated brine water solution (15 mL), dried over anhydrous Na$_2$SO$_4$ and evaporated. The residue was purified by column chromatography (silica gel, petroleum ether/EtOAc=10:1-2:1) to afford the titled compound II (135 mg, 27%) as a white solid. $^1$H-NMR (400 MHz, DMSO-d6) δ=7.90 (br. s, 2H), 7.87 (s, 1H), 7.73 (d, J=2.4 Hz, 1H), 7.50 (dd, J=2.0, 8.8 Hz, 1H); MS (ESI): [M+H$^+$]=276.8.

Example 3

6-(Pentafluorosulfanyl)benzo[d]oxazol-2-amine (III)

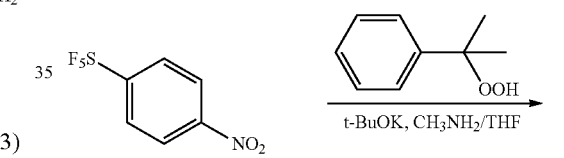

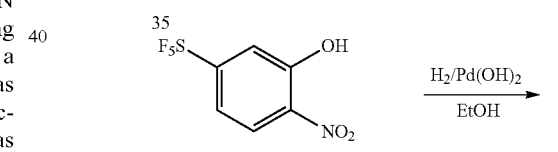

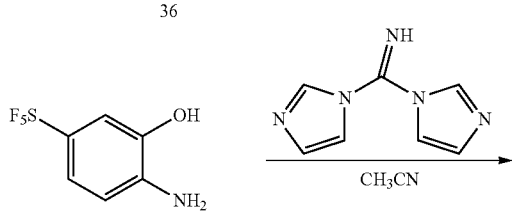

Step 1: 2-Nitro-5-(pentafluorosulfanyl)phenol (36)

To a stirred solution of t-BuOK (337 mg, 3 mmol) in CH$_3$NH$_2$ (2 M in THF, 5 mL) at −50° C. was added dropwise a solution of 1-nitro-4-(pentafluorosulfanyl)benzene (35)

(249 mg, 1 mmol) and cumene hydroperoxide (80%, 0.2 mL, 1.1 mmol) in dry THF (1 mL). The resulting brown mixture was stirred at −50° C. for 15 min followed by the addition of solid NH$_4$Cl (1 g) and evaporation of CH$_3$NH$_2$. The resulting mixture was treated with aqueous HCl (1 M) to pH 1 and extracted with CH$_2$Cl$_2$ (3×20 mL). The combined organic extracts were washed with aqueous NaOH (0.5 M, 3×15 mL), the alkaline extracts were collected and acidified with aqueous HCl (6 M) until pH 1, and then extracted with CH$_2$Cl$_2$ (3×20 mL). The combined organic phase was dried over anhydrous MgSO$_4$ and evaporated. The residue was purified by column chromatography (silica gel, petroleum ether/EtOAc=20:1) to afford the titled compound 36 (238 mg, 90%) as a yellow oil. $^1$H-NMR (400 MHz, CDCl$_3$) δ=10.56 (br. s, 1H), 8.23 (d, J=9.2 Hz, 1H), 7.62 (d, J=2.4 Hz, 1H), 7.40 (dd, J=2.4, 9.6 Hz, 1H).

Step 2: 2-Amino-5-(pentafluorosulfanyl)phenol (37)

To a solution of 2-nitro-5-(pentafluorosulfanyl)phenol (36) (616 mg, 2.32 mmol) in ethanol (5 mL) was added Pd(OH)$_2$ (200 mg, 10% on charcoal). The mixture was stirred under H$_2$ atmosphere for 3 h. The mixture was filtered and the filtrate was concentrated to give the titled compound 37 (448 mg, 82%) as a yellow oil. $^1$H-NMR (400 MHz, CDCl$_3$) δ=7.21 (dd, J=2.0, 8.4 Hz, 1H), 7.12 (d, J=2.0 Hz, 1H), 6.67 (d, J=8.8 Hz, 1H), 4.88 (br. s, 1H), 4.08 (br. s, 2H).

Step 3: 6-(Pentafluorosulfanyl)benzo[d]oxazol-2-amine (III)

To a stirred solution of 2-amino-5-(pentafluorosulfanyl) phenol (37) (410 mg, 1.74 mmol) in CH$_3$CN (10 mL) was added di(1H-imidazol-1-yl)methanimine (562 mg, 3.49 mmol) in one portion at 20° C. The reaction mixture was stirred at 80° C. for 6 h. The solvent was evaporated and the residue was purified by column chromatography (silica gel, petroleum ether/EtOAc=10:1-2:1) to afford the titled compound III (296 mg, 65%) as a white solid. $^1$H-NMR (400 MHz, DMSO-d6) δ=7.99 (d, J=2.0 Hz, 1H), 7.96 (s, 2H), 7.64 (dd, J=2.0, 8.4 Hz, 1H), 7.30 (d, J=8.8 Hz, 1H); MS (ESI): [M+H$^+$]=260.7.

Example 4

5-(Pentafluorosulfanyl)benzo[d]oxazol-2-amine (IV)

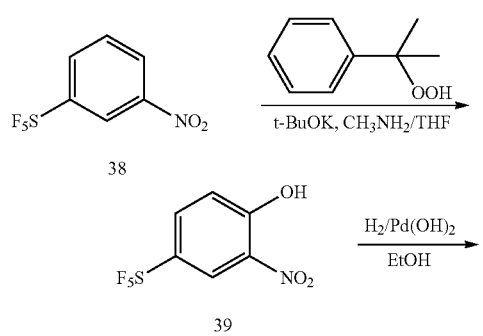

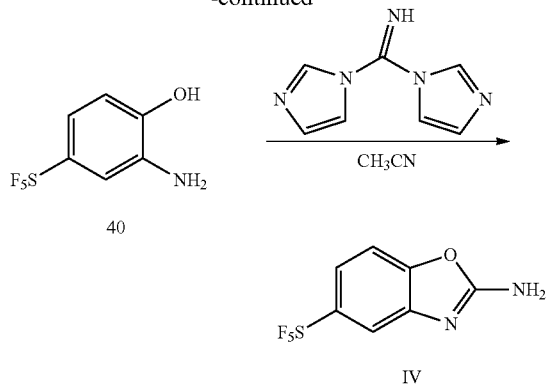

Step 1: 2-Nitro-4-(pentafluorosulfanyl)phenol (39)

To a stirred solution of t-BuOK (100 mg, 3 mmol) in CH$_3$NH$_2$ (2 M in THF, 2 mL) at −50° C. was added dropwise a solution of 1-nitro-4-(pentafluorosulfanyl)benzene (38) (249 mg, 1 mmol) and cumene hydroperoxide (80%, 84 mg, 1.1 mmol) in dry THF (1 mL). The resulting brown mixture was stirred at −50° C. for 15 min followed by the addition of solid NH$_4$Cl (1 g) and evaporation of CH$_3$NH$_2$. The resulting mixture was treated with aqueous HCl (1 M) to pH 1 and extracted with DCM (3×20 mL). The combined organic extracts were washed with aqueous NaOH (0.5 M, 3×15 mL), the alkaline solutions were collected and acidified with aqueous HCl (6 M) until pH 1, and then extracted with CH$_2$Cl$_2$ (3×20 mL). The combined organic phase was dried over anhydrous MgSO$_4$ and evaporated. The crude product 39 was obtained as a yellow oil (265 mg, 100%), which was used for the next step without further purification. $^1$H-NMR (400 MHz, CDCl$_3$) δ=10.78 (br. s, 1H), 8.57 (s, 1H), 7.96 (d, J=8.4 Hz, 1H), 7.51 (s, 1H).

Step 2: 2-Amino-4-(pentafluorosulfanyl)phenol (40)

To a solution of 2-nitro-4-(pentafluorosulfanyl)phenol (39) (150 mg, 0.40 mmol) in ethanol (3 mL) was added Pd(OH)$_2$ (80 mg, 10% on charcoal). The mixture was stirred under H$_2$ atmosphere for 3 h. The mixture was filtered and the filtrate was concentrated to give the crude product, which was purified by prep-TLC (silica gel, petroleum ether/ EtOAc=3:1) to afford the titled compound 40 (70 mg, 74%) as a yellow oil. $^1$H-NMR (400 MHz, CDCl$_3$) δ=7.14 (d, J=2.4 Hz, 1H), 7.07 (dd, J=2.0, 8.8 Hz, 1H), 6.72 (d, J=8.8 Hz, 1H), 5.40 (br. s, 1H); MS (ESI): [M+H$^+$]=235.8.

Step 3: 5-(Pentafluorosulfanyl)benzo[d]oxazol-2-amine (IV)

To a stirred solution of 2-amino-4-(pentafluorosulfanyl) phenol (40) (70 mg, 0.30 mmol) in CH$_3$CN (1 mL) was added di(1H-imidazol-1-yl)methanimine (96 mg, 0.60 mmol) in one portion at 20° C. The reaction mixture was stirred at 80° C. for 6 h. The solvent was evaporated and the residue was purified by column chromatography (silica gel, petroleum ether/EtOAc=10:1-2:1) to afford the titled compound IV (56 mg, 72%) as a white solid. $^1$H-NMR (400 MHz, DMSO-d6) δ=7.85 (s, 2H), 7.68 (s, 1H), 7.52 (s, 1H); MS (ESI): [M+H$^+$]=260.8.

Example 5

6-(Pentafluorosulfanyl)benzo[d][1,3]selenazol-2-amine (V)

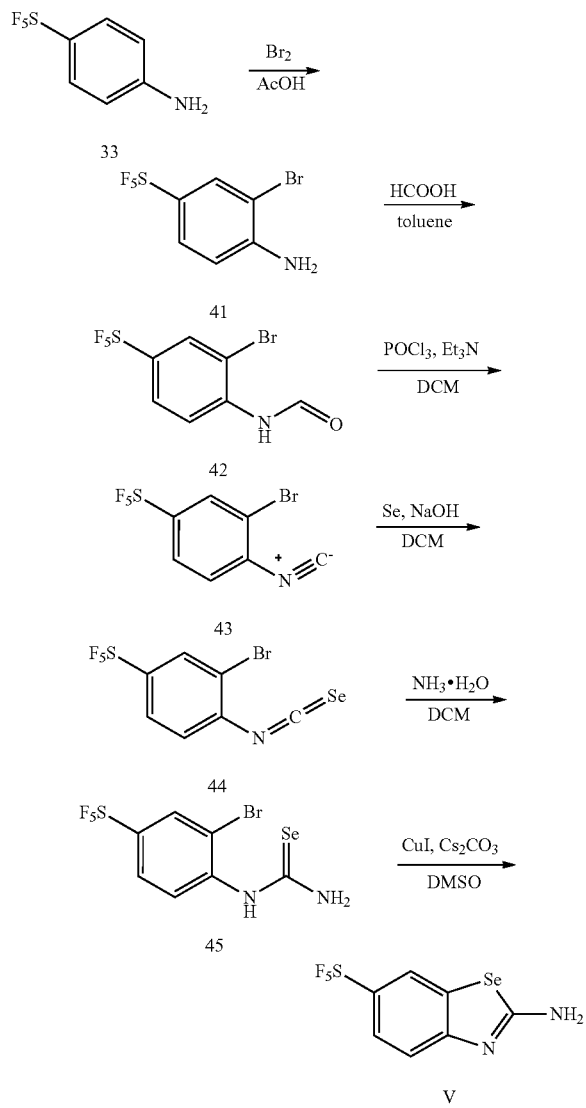

Step 1: 2-Bromo-4-(pentafluorosulfanyl)aniline (41)

To a stirred solution of 4-(pentafluorosulfanyl)aniline (33) (500.0 mg, 2.28 mmol) in AcOH (5.0 mL) was added a solution of $Br_2$ (364.6 mg, 2.28 mmol) in AcOH (1.0 mL) slowly at 10° C. The mixture was stirred at 10° C. for 3 h. The mixture was quenched with ice-water (60 mL), extracted with EtOAc (2×30 mL), combined extracts dried over anhydrous $Na_2SO_4$ and concentrated. The residue was purified by column chromatography (silica gel, petroleum ether/EtOAc=20:1-10:1) to afford the titled compound 41 (648 mg, 96%) as a yellow solid. $^1$H-NMR (400 MHz, $CDCl_3$) δ=7.81 (d, J=2.4 Hz, 1H), 7.49 (dd, J=2.4, 9.2 Hz, 1H), 6.71 (d, J=9.2 Hz, 1H), 4.46 (s, 2H).

Step 2: N-(2-bromo-4-(pentafluorosulfanyl)phenyl)formamide (42)

To a stirred solution of 2-bromo-4-(pentafluorosulfanyl) aniline (41) (1.54 g, 5.17 mmol) in dry toluene (20 mL) was added HCOOH (4.0 mL, 103.30 mmol) dropwise at 20° C. The reaction was stirred at 100° C. for 16 h. After that, the reaction mixture was cooled to 30° C., diluted with EtOAc (60 mL), successively washed with water (30 mL) and saturated brine water solution (30 mL), dried over anhydrous $Na_2SO_4$ and concentrated. The residue was purified by column chromatography (silica gel, petroleum ether/EtOAc=20:1-5:1) to afford the titled compound 42 (1.63 g, 97%) as a yellow solid. $^1$H-NMR (400 MHz, DMSO-d6) δ=10.07 (s, 1H), 8.44 (s, 1H), 8.39 (d, J=8.8 Hz, 1H), 8.22 (d, J=2.4 Hz, 1H), 7.96 (dd, J=2.4, 8.8 Hz, 1H).

Step 3: 2-Bromo-1-isocyano-4-(pentafluorosulfanyl)benzene (43)

To a solution of N-(2-bromo-4-(pentafluorosulfanyl)phenyl)formamide (42) (400 mg, 1.23 mmol) in dry $CH_2Cl_2$ (10 mL) was added $Et_3N$ (0.5 mL, 3.68 mmol) at 0° C. followed by $POCl_3$ (282 mg, 1.84 mmol). The reaction was stirred under 0° C.-20° C. for 3 h. After that, saturated aqueous $Na_2CO_3$ solution was added slowly. After stirring for 30 min, the aqueous phase was extracted with $CH_2Cl_2$ (2×20 mL). The combined organic phases dried over anhydrous $Na_2SO_4$ and concentrated. The residue was purified by column chromatography (silica gel, petroleum ether/EtOAc=50:1-20:1) to give the titled compound 43 (236 mg, 62%) as a dark oil. $^1$H-NMR (400 MHz, $CDCl_3$) δ=8.08 (d, J=2.0 Hz, 1H), 7.78 (dd, J=2.0, 8.8 Hz, 1H), 7.56 (d, J=8.8 Hz, 1H).

Step 4: 2-Bromo-1-isoselenocyanato-4-(pentafluorosulfanyl)benzene (44)

To a suspension of 2-bromo-1-isocyano-4-(pentafluorosulfanyl)benzene (43) (517 mg, 1.68 mmol) in $CH_2Cl_2$ (10 mL) was added Se power (398 mg, 5.03 mmol), benzyltriethylammonium chloride (19.10 mg, 0.084 mmol), followed by addition of aqueous NaOH solution (50%, 0.5 mL). The reaction was stirred at 40° C. for 3 h. After that, the reaction mixture was diluted with $CH_2Cl_2$ (20 mL), washed with water (10 mL) and saturated brine water solution (10 mL) successively, dried over anhydrous $Na_2SO_4$ and concentrated. The residue was purified by column chromatography (silica gel, petroleum ether/EtOAc=50:1-20:1) to afford the titled compound 44 (308 mg, 47%) as a yellow oil. $^1$H-NMR (400 MHz, $CDCl_3$) δ=8.00 (d, J=2.4 Hz, 1H), 7.71 (dd, J=2.4, 9.2 Hz, 1H), 7.39 (d, J=8.8 Hz, 1H).

Step 5: 1-(2-Bromo-4-(pentafluorosulfanyl)phenyl)selenourea (45)

To a suspension of 2-bromo-1-isoselenocyanato-4-(pentafluorosulfanyl)benzene (44) (308 mg, 0.80 mmol) in $CH_2Cl_2$ (6 mL) was added $NH_4OH$ (134 mg, 25% in water) at 20° C. The mixture was stirred at 20° C. for 15 min. The solvents in the mixture were evaporated to give the titled compound 45 (322 mg, 100%) as a white solid. $^1$H-NMR (400 MHz, DMSO-d6) δ=9.88 (s, 1H), 8.64 (s, 1H), 8.19 (d, J=2.0 Hz, 1H), 7.96 (br. s, 1H), 7.90 (dd, J=2.4, 8.8 Hz, 1H), 7.78 (d, J=8.4 Hz, 1H).

Step 6: 6-(Pentafluorosulfanyl)benzo[d][1,3]selenazol-2-amine (V)

To a stirred solution of 1-(2-bromo-4-(pentafluorosulfanyl)phenyl)selenourea (45) (322 mg, 0.80 mmol) in DMSO (6 mL) was added CuI (15 mg, 0.08 mmol), 1,10-phenanathroline (14 mg, 0.08 mmol) at 20° C., followed by addition of $Cs_2CO_3$ (130 mg, 0.40 mmol). The reaction was stirred at 80° C. under nitrogen for 30 min. After that, the reaction mixture was quenched with ice-water (60 mL), extracted with EtOAc (2×30 mL). The combined organic phase was washed with saturated brine water solution (30 mL), dried over anhydrous $Na_2SO_4$ and concentrated. The residue was purified by prep-HPLC to afford the titled compound V (15 mg, 6%) as a white solid. $^1$H-NMR (400 MHz, DMSO-d6) δ=8.30 (d, J=2.4 Hz, 1H), 8.00 (s, 2H), 7.64 (dd, J=2.4, 8.8 Hz, 1H), 7.33 (d, J=8.8 Hz, 1H); MS (ESI): [M+H$^+$]=324.7.

Example 6

6-(Trifluoromethyl)benzo[d][1,3]selenazol-2-amine (VI)

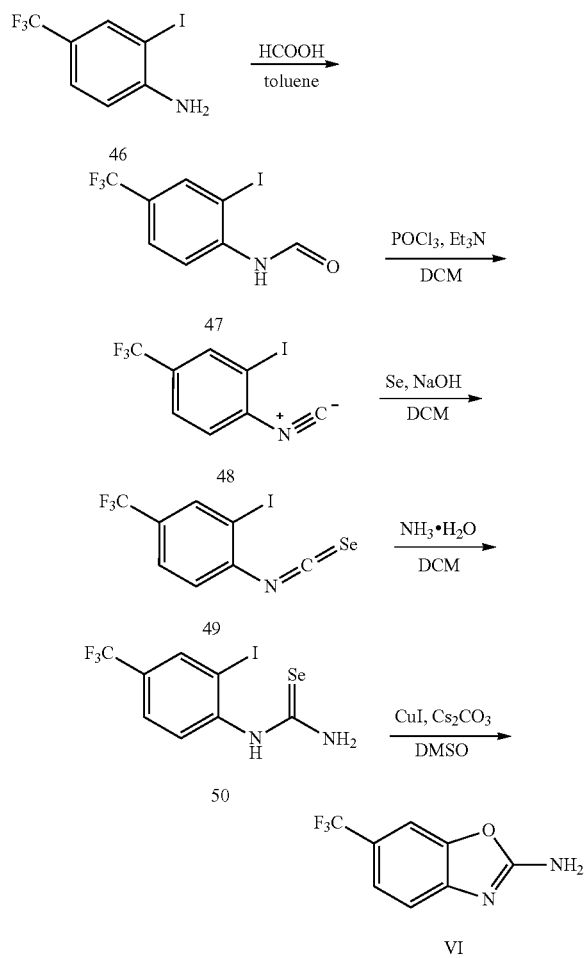

Step 1: N-(2-iodo-4-(trifluoromethyl)phenyl)formamide (47)

To a stirred solution of 2-iodo-4-(trifluoromethyl)aniline (46) (3.0 g, 10.5 mmol) in dry toluene (30 mL) was added HCOOH (4.0 mL, 114.5 mmol) dropwise at 20° C. The reaction was stirred at 100° C. for 16 h. The mixture was cooled to 30° C., diluted with EtOAc (80 mL), washed with water (40 mL) and saturated brine water solution (40 mL) successively, dried over anhydrous $Na_2SO_4$ and concentrated. The residue was purified by column chromatography (silica gel, petroleum ether/EtOAc=20:1-10:1) to give the titled compound 47 (3.1 g, 94%) as a white solid. MS (ESI): [M+H$^+$]=315.7

Step 2: 2-Iodo-1-isocyano-4-(trifluoromethyl)benzene (48)

To a solution of N-(2-iodo-4-(trifluoromethyl)phenyl)formamide (47) (2.0 g, 6.35 mmol) in dry $CH_2Cl_2$ (30 mL) was added $Et_3N$ (2.6 mL, 19.05 mmol) at 0° C., followed by addition of $POCl_3$ (1.5 g, 9.52 mmol). The reaction was stirred at 0-20° C. for 3 h, followed by dropwise addition of aqueous saturated $Na_2CO_3$ solution (10 mL). After stirring for 30 min, the aqueous phase was extracted with DCM (2×30 mL). The combined organic phase dried over anhydrous $Na_2SO_4$ and concentrated. The residue was purified by column chromatography (silica gel, petroleum ether/EtOAc=50:1-20:1) to give the titled compound 48 (1.32 g, 70%) as a dark oil.

Step 3: 2-Iodo-1-isoselenocyanato-4-(trifluoromethyl)benzene (49)

To a suspension of 2-iodo-1-isocyano-4-(trifluoromethyl)benzene (48) (1.32 g, 4.44 mmol) in $CH_2Cl_2$ (30 mL) was added Se power (1.05 g, 13.33 mmol), benzyltriethylammonium chloride (50.70 mg, 0.22 mmol) and aqueous NaOH solution (50%, 2.0 mL). The reaction was stirred at 40° C. for 3 h. The mixture was diluted with $CH_2Cl_2$ (30 mL), washed with water (20 mL) and saturated brine water solution (20 mL) successively, dried over anhydrous $Na_2SO_4$ and concentrated. The residue was purified by column chromatography (silica gel, PE/EA=50:1-20:1) to give the titled compound 49 (0.90 g, 54%) as a yellow oil. $^1$H-NMR (400 MHz, CDCl$_3$) δ=8.08 (s, 1H), 7.61 (d, J=8.0 Hz, 1H), 7.40 (d, J=8.4 Hz, 1H).

Step 4: 1-(2-Iodo-4-(trifluoromethyl)phenyl)selenourea (50)

To a suspension of 2-iodo-1-isoselenocyanato-4-(trifluoromethyl)benzene (49) (300 mg, 0.80 mmol) in $CH_2Cl_2$ (6 mL) was added $NH_4OH$ (134 mg, 25% in water) at 20° C. The reaction was stirred at 20° C. for 15 min. The solvents were evaporated to give the titled compound 50 (314 mg, 100%) as a white solid. $^1$H-NMR (40 0 MHz, DMSO-d6) δ=9.79 (s, 1H), 8.48 (s, 1H), 8.16 (s, 1H), 7.76 (s, 1H), 7.73 (d, J=8.0 Hz, 1H), 7.57 (d, J=8.4 Hz, 1H).

Step 5: 6-(Trifluoromethyl)benzo[d][1,3]selenazol-2-amine (VI)

To a stirred solution of 1-(2-iodo-4-(trifluoromethyl)phenyl)selenourea (50) (600.0 mg, 1.53 mmol) in DMSO (10 mL) was added CuI (29.1 mg, 0.15 mmol), 1,10-phenanathroline (27.5 mg, 0.15 mmol) and $Cs_2CO_3$ (248.0 mg, 0.76 mmol) at 20° C. The reaction was stirred at 80° C. under nitrogen for 30 min. The mixture was quenched with ice-water (60 mL), extracted with EtOAc (2×30 mL). The combined organic phase was washed with saturated brine water solution (30 mL), dried over anhydrous $Na_2SO_4$ and concentrated. The residue was purified by column chromatography (silica gel, petroleum ether/EtOAc=10:1-2:1) to afford the titled compound VI (226 mg, 56%) as a light yellow solid. $^1$H-NMR (400 MHz, DMSO-d6) δ=8.12 (d, J=1.2 Hz, 1H), 7.94 (s, 2H), 7.48 (dd, J=1.2, 8.8 Hz, 1H), 7.40 (d, J=8.8 Hz, 1H); MS (ESI): [M+H$^+$]=266.7.

Example 7

6-(Trifluoromethoxy)benzo[d][1.3]selenazol-2-amine (VII)

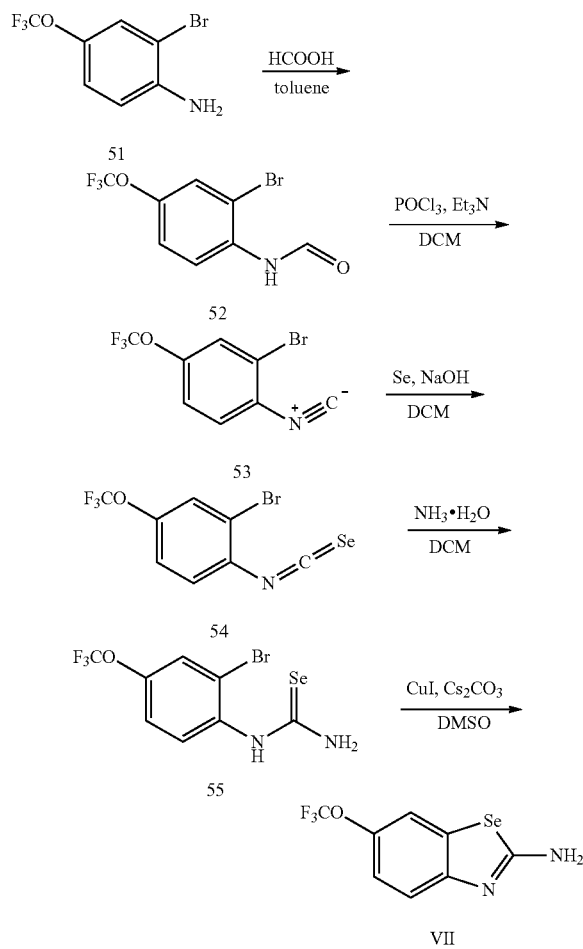

Step 1:
N-(2-bromo-4-(trifluoromethoxy)phenyl)formamide (52)

To a stirred solution of 2-bromo-4-(trifluoromethoxy) aniline (51) (3.0 g, 11.7 mmol) in dry toluene (30 mL) was added HCOOH (4.3 mL, 113.7 mmol) dropwise at 20° C. The reaction was stirred at 100° C. for 16 h. The mixture was cooled to 30° C., diluted with EtOAc (60 mL), washed with water (30 mL) and saturated brine water solution (30 mL) successively, dried over anhydrous Na$_2$SO$_4$ and concentrated. The residue was purified by column chromatography (silica gel, petroleum ether/EtOAc=20:1-5:1) to afford the titled compound 52 (3.2 g, 96%) as a white solid. $^1$H-NMR (400 MHz, DMSO-d6) δ=9.90 (s, 1H), 8.37 (s, 1H), 8.14 (d, J=8.8 Hz, 1H), 7.78 (d, J=2.0 Hz, 1H), 7.45 (d, J=8.8 Hz, 1H).

Step 2:
2-Bromo-1-isocyano-4-(trifluoromethoxy)benzene (53)

To a solution of N-(2-bromo-4-(trifluoromethoxy)phenyl) formamide (52) (2.0 g, 7.04 mmol) in dry CH$_2$Cl$_2$ (30 mL) was added Et$_3$N (2.1 g, 21.12 mmol) at 0° C., followed by addition of POCl$_3$ (1.6 g, 10.56 mmol). The reaction was stirred at 0-20° C. for 3 h, followed by dropwise addition of aqueous saturated Na$_2$CO$_3$ solution (10 mL). After stirring for 30 min, the mixture was extracted with CH$_2$Cl$_2$ (2×30 mL). The aqueous phase dried over anhydrous Na$_2$SO$_4$ and concentrated. The residue was purified by column chromatography (silica gel, petroleum ether/EtOAc=50:1-20:1) to afford the titled compound 53 (1.8 g, 96%) as a dark oil. $^1$H-NMR (400 MHz, CDCl$_3$) δ=7.55 (d, J=1.6 Hz, 1H), 7.51 (d, J=9.2 Hz, 1H), 7.24 (dd, J=1.6, 9.2 Hz, 1H).

Step 3: 2-Bromo-1-isoselenocyanato-4-(trifluoromethoxy)benzene (54)

To a suspension of 2-bromo-1-isocyano-4-(trifluoromethoxy)benzene (53) (1.80 g, 6.77 mmol) in CH$_2$Cl$_2$ (36 mL) was added Se power (1.60 g, 20.30 mmol), benzyltriethylammonium chloride (77.52 mg, 0.34 mmol), followed by addition of aqueous NaOH solution (50%, 5 mL). The reaction was stirred at 40° C. for 3 h. The mixture was diluted with CH$_2$Cl$_2$ (50 mL), washed with water (30 mL) and saturated brine water solution (30 mL) successively, dried over anhydrous Na$_2$SO$_4$ and concentrated. The residue was purified by column chromatography (silica gel, petroleum ether/EtOAc=50:1-20:1) to give the titled compound 54 (0.95 g, 41%) as a colorless solid. $^1$H-NMR (400 MHz, CDCl$_3$) δ=7.49 (d, J=2.0 Hz, 1H), 7.36 (d, J=8.8 Hz, 1H), 7.18 (dd, J=1.2, 8.4 Hz, 1H).

Step 4:
1-(2-Bromo-4-(trifluoromethoxy)phenyl)selenourea (55)

To a suspension of 2-bromo-1-isoselenocyanato-4-(trifluoromethoxy)benzene (54) (820 mg, 2.38 mmol) in CH$_2$Cl$_2$ (10 mL) was added NH$_4$OH (400 mg, 25% in water) at 20° C. The reaction was stirred at 20° C. for 15 min. The solvents were evaporated to give the titled compound 55 (862 mg, 100%) as an off-white solid. $^1$H-NMR (400 MHz, DMSO-d6) δ=9.78 (s, 1H), 8.45 (s, 1H), 7.76 (d, J=2.0 Hz, 1H), 7.74 (br. s, 1H), 7.56 (d, J=9.2 Hz, 1H), 7.42 (dd, J=1.2, 8.4 Hz, 1H).

Step 5: 6-(Trifluoromethoxy)benzo[d][1,3]selenazol-2-amine (VII)

To a stirred solution of 1-(2-bromo-4-(trifluoromethoxy) phenyl)selenourea (55) (600.0 mg, 1.66 mmol) in DMSO (10 mL) was added CuI (31.6 mg, 0.17 mmol), 1,10-phenanathroline (30.0 mg, 0.17 mmol) at 20° C., followed by addition of Cs$_2$CO$_3$ (270.0 mg, 0.83 mmol). The reaction was stirred at 80° C. under nitrogen for 30 min. The mixture was quenched with ice-water (60 mL), extracted with EA (2×30 mL). The combined organic phase was washed saturated brine water solution (30 mL), dried over anhydrous Na$_2$SO$_4$ and concentrated. The residue was purified by column chromatography (silica gel, petroleum ether/EtOAc=10:1-2:1) to afford the titled compound VII (106 mg, 23%) as a white solid. $^1$H-NMR (400 MHz, DMSO-d6) δ=7.77 (d, J=1.2 Hz, 1H), 7.71 (s, 2H), 7.33 (d, J=8.8 Hz, 1H), 7.16 (dd, J=1.2, 8.4 Hz, 1H); MS (ESI): [M+H$^+$]= 282.8.

Example 8

5-(Trifluoromethyl)benzo[d][1,3]selenazol-2-amine (VIII)

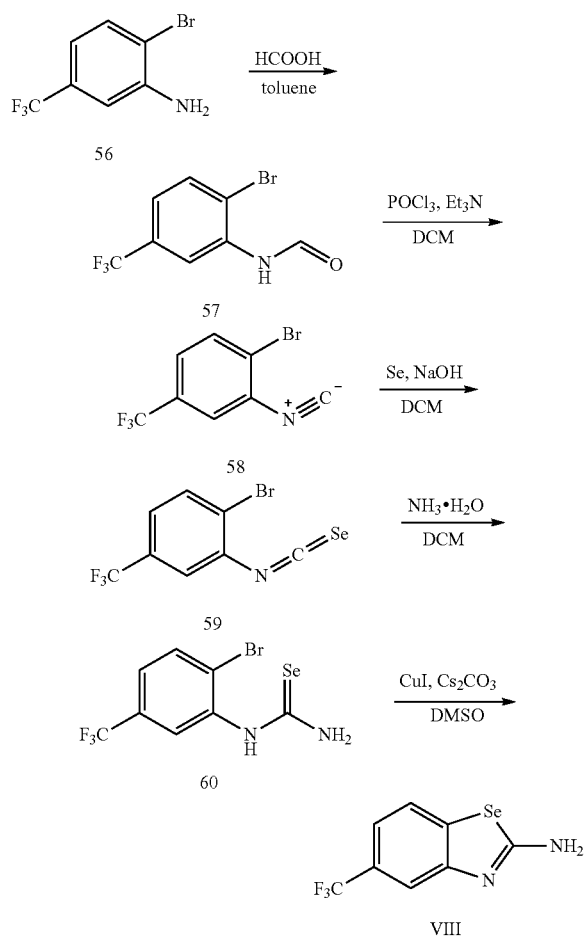

Step 1: N-(2-bromo-5-(trifluoromethyl)phenyl)formamide (57)

To a stirred solution of 2-bromo-5-(trifluoromethyl)aniline (56) (4.0 g, 16.67 mmol) in dry toluene (40 mL) was added HCOOH (6.4 mL, 166.70 mmol) dropwise at 20° C. The reaction was stirred at 100° C. for 16 h. The mixture was cooled to 30° C., diluted with EtOAc (120 mL), washed with (30 mL) and saturated brine water solution (30 mL) successively, dried over anhydrous Na$_2$SO$_4$ and concentrated. The residue was purified by column chromatography (silica gel, petroleum ether/EtOAc=20:1-10:1) to afford the titled compound 57 (4.2 g, 93%) as a white solid. $^1$H-NMR (400 MHz, DMSO-d6) δ=10.05 (s, 1H), 8.48 (s, 1H), 8.42 (s, 1H), 7.92 (d, J=8.4 Hz, 1H), 7.43 (d, J=8.4 Hz, 1H); MS (ESI): [M+H$^+$+CH$_3$CN]=310.8.

Step 2: 2-Bromo-1-isocyano-5-(trifluoromethyl)benzene (58)

To a solution of N-(2-bromo-5-(trifluoromethyl)phenyl) formamide (57) (3.0 g, 11.19 mmol) in dry CH$_2$Cl$_2$ (40 mL) was added Et$_3$N (4.7 mL, 33.58 mmol) at 0° C., followed by addition of POCl$_3$ (2.6 g, 16.79 mmol). The reaction was stirred at 0° C.-20° C. for 3 h, followed by dropwise addition of aqueous saturated Na$_2$CO$_3$ solution. After stirring for 30 min, the mixture was extracted with CH$_2$Cl$_2$ (2×50 mL) The combined organic phase dried over anhydrous Na$_2$SO$_4$ and concentrated. The residue was purified by column chromatography (silica gel, petroleum ether/EtOAc=50:1-20:1) to afford the titled compound 58 (2.02 g, 68%) as a dark oil. $^1$H-NMR (400 MHz, CDCl$_3$) δ=7.83 (d, J=8.0 Hz, 1H), 7.71 (s, 1H), 7.54 (d, J=8.4 Hz, 1H).

Step 3: 2-Bromo-1-isoselenocyanato-5-(trifluoromethyl)benzene (59)

To a suspension of 2-bromo-1-isocyano-5-(trifluoromethyl)benzene (58) (2.0 g, 8.08 mmol) in CH$_2$Cl$_2$ (40 mL) was added Se power (1.92 g, 24.24 mmol), benzyltriethylammonium chloride (92 mg, 0.40 mmol), followed by addition of aqueous NaOH solution (50%, 4.0 mL). The mixture was stirred at 40° C. for 3 h. The mixture was diluted with CH$_2$Cl$_2$ (100 mL), washed with water (50 mL) and saturated brine water solution (50 mL) successively, dried over anhydrous Na$_2$SO$_4$ and concentrated. The residue was purified by column chromatography (silica gel, petroleum ether/EtOAc=50:1-20:1) to give the titled compound 59 (1.56 g, 54%) as a yellow oil. $^1$H-NMR (400 MHz, CDCl$_3$) δ=7.75 (d, J=8.4 Hz, 1H), 7.56 (s, 1H), 7.42 (d, J=8.4 Hz, 1H).

Step 4: 1-(2-Bromo-5-(trifluoromethyl)phenyl)selenourea (60)

To a suspension of 2-bromo-1-isoselenocyanato-5-(trifluoromethyl)benzene (59) (580 mg, 1.76 mmol) in CH$_2$Cl$_2$ (10 mL) was added NH$_4$OH (0.33 mL, 25% in water) at 20° C. The reaction was stirred at 20° C. for 15 min. The solvents were evaporated to give the titled compound 60 (593 mg, 97%) as a white solid. $^1$H-NMR (400 MHz, DMSO-d6) δ=9.87 (s, 1H), 8.53 (s, 1H), 7.90 (d, J=8.4 Hz, 2H), 7.86 (s, 1H), 7.55 (dd, J=1.5, 8.0 Hz, 1H); MS (ESI): [M+H$^+$]= 346.7.

Step 5: 5-(Trifluoromethyl)benzo[d][1,3]selenazol-2-amine (VIII)

To a stirred solution of 1-(2-bromo-5-(trifluoromethyl) phenyl)selenourea (60) (500.0 mg, 1.53 mmol) in DMSO (10 mL) was added CuI (27.5 mg, 0.14 mmol), 1,10-phenanathroline (26.0 mg, 0.14 mmol) at 20° C., followed by addition of Cs$_2$CO$_3$ (235.4 mg, 0.72 mmol). The reaction was stirred at 80° C. under nitrogen for 30 min. The mixture was quenched with ice-water (60 mL), extracted with EA (2×40 mL). The combined organic phase was washed with saturated brine water solution (50 mL), dried over anhydrous Na$_2$SO$_4$ and concentrated. The residue was purified by prep-HPLC (0.5% TFA in eluents) to afford the titled compound VIII (200 mg, 52%) as a light yellow solid. $^1$H-NMR (400 MHz, DMSO-d6) δ=8.39 (br. s, 2H), 7.98 (d, J=8.0 Hz, 1H), 7.57 (s, 1H), 7.31 (d, J=8.0 Hz, 1H); MS (ESI): [M+H$^+$]=266.7.

Example 9

6-((Trifluoromethyl)thio)benzo[d][1,3]selenazol-2-amine (IX)

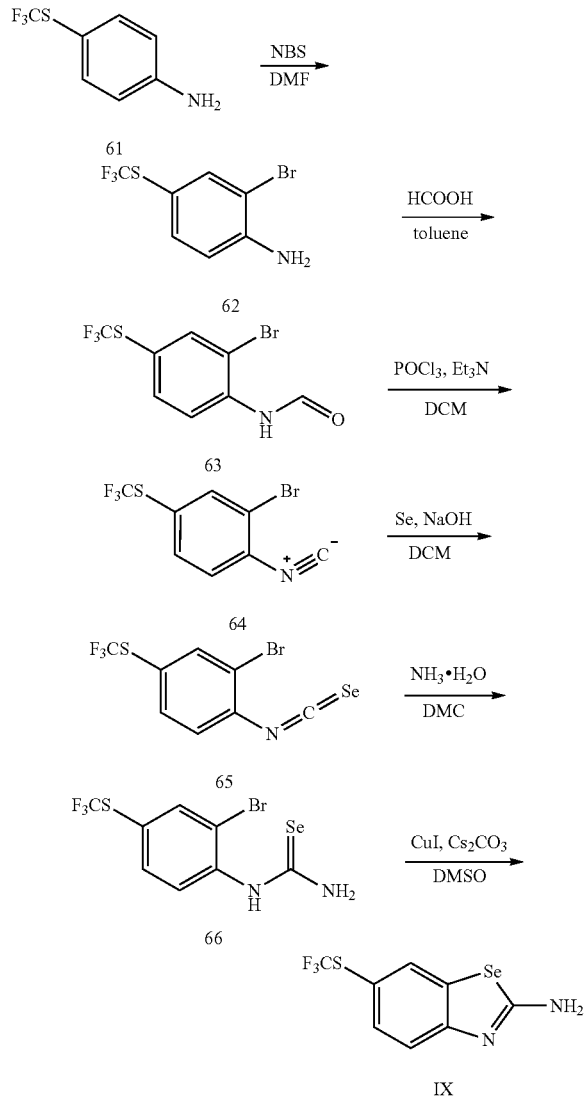

Step 1: 2-Bromo-4-((trifluoromethyl)thio)aniline (62)

To a stirred solution of 4-((trifluoromethyl)thio)aniline (61) (4.0 g, 20.72 mmol) in DMF (40 mL) was added N-bromosuccinamide (NBS) (3.87 g, 21.74 mmol). The mixture was stirred at 30° C. for 2 h. The mixture was quenched with ice-water (120 mL), extracted with EtOAc (2×50 mL). The combined organic phase was washed with water (50 mL) and saturated brine water solution (50 mL) successively, dried over anhydrous Na$_2$SO$_4$ and concentrated. The residue was purified by column chromatography (silica gel, petroleum ether/EtOAc=20:1-10:1) to afford the titled compound 62 (3.60 g, 64%) as a red oil $^1$H-NMR (400 MHz, CDCl$_3$) δ=7.70 (d, J=1.6 Hz, 1H), 7.37 (dd, J=1.6, 8.0 Hz, 1H), 6.75 (d, J=8.4 Hz, 1H), 4.41 (br. s, 2H); MS (ESI): [M+H$^+$]=273.8.

Step 2: N-(2-bromo-4-((trifluoromethyl)thio)phenyl)formamide (63)

To a stirred solution of 2-bromo-4-((trifluoromethyl)thio) aniline (62) (3.0 g, 11.03 mmol) in dry toluene (30 mL) was added HCOOH (4.3 mL, 113.70 mmol) dropwise at 20° C. The reaction was stirred at 100° C. for 16 h. The mixture was cooled to 30° C., diluted with EtOAc (60 mL), washed with water (50 mL) and brine (50 mL) successively. The organic phase was dried over anhydrous Na$_2$SO$_4$ and concentrated. The residue was purified by column chromatography (silica gel, petroleum ether/EtOAc=20:1-5:1) to afford the titled compound 63 (3.1 g, 94%) as a white solid. $^1$H-NMR (400 MHz, DMSO-d6) δ=10.00 (s, 1H), 8.42 (s, 1H), 8.29 (d, J=8.4 Hz, 1H), 8.03 (d, J=1.6 Hz, 1H), 7.74 (dd, J=1.2, 8.4 Hz, 1H); MS (ESI): [M+H$^+$+CH$_3$CN]=340.8.

Step 3: (3-Bromo-4-isocyanophenyl)(trifluoromethyl)sulfane (64)

To a solution of N-(2-bromo-4-((trifluoromethyl)thio) phenyl)formamide (63) (3.00 g, 10.0 mmol) in dry CH$_2$Cl$_2$ (30 mL) was added Et$_3$N (4.17 mL, 30.0 mmol) at ice-bath, followed by addition of POCl$_3$ (1.40 mL, 15.0 mmol). The reaction was stirred under 0° C.-20° C. for 3 h, followed by dropwise addition of saturated aqueous Na$_2$CO$_3$ solution (10 mL). After stirring for 30 min, the mixture was extracted with CH$_2$Cl$_2$ (2×30 mL) The combined organic phase dried over anhydrous Na$_2$SO$_4$ and concentrated. The residue was purified by column chromatography (silica gel, petroleum ether/EtOAc=50:1-20:1) to afford the titled compound 64 (2.4 g, 84%) as a dark solid. $^1$H-NMR (400 MHz, CDCl$_3$) δ=7.97 (d, J=1.6 Hz, 1H), 7.65 (dd, J=1.6, 8.0 Hz, 1H), 7.49 (d, J=8.8 Hz, 1H).

Step 4: (3-Bromo-4-isoselenocyanatophenyl)(trifluoromethyl)sulfane (65)

To a suspension of (3-bromo-4-isocyanophenyl)(trifluoromethyl)sulfane (64) (800 mg, 2.84 mmol) in CH$_2$Cl$_2$ (8 mL) was added Se power (672 mg, 8.51 mmol), benzyltriethylammonium chloride (33 mg, 0.14 mmol), followed by addition of aqueous NaOH solution (50%, 1.2 mL). The reaction was stirred at 40° C. for 2 h. After that, the reaction mixture was diluted with CH$_2$Cl$_2$ (50 mL). The organic phase was washed with water (50 mL) and brine (50 mL) successively, dried over anhydrous Na$_2$SO$_4$ and concentrated. The residue was purified by column chromatography (silica gel, petroleum ether/EtOAc=50:1-20:1) to afford the titled compound 65 (0.78 g, 78%) as a brown solid. $^1$H-NMR (400 MHz, CDCl$_3$) δ=7.90 (d, J=1.6 Hz, 1H), 7.60 (dd, J=1.6, 8.0 Hz, 1H), 7.36 (d, J=8.8 Hz, 1H).

Step 5: 1-(2-Bromo-4-((trifluoromethyl)thio)phenyl) selenourea (66)

To a solution of (3-bromo-4-isoselenocyanatophenyl)(trifluoromethyl)sulfane (65) (558 mg, 1.55 mmol) in CH$_2$Cl$_2$ (6 mL) was added NH₄OH (0.3 mL, 25% in water) at 20° C. The reaction was stirred at 20° C. for 30 min. The solvents were evaporated to give the titled compound 66 (486 mg, 83%) as a yellow solid. $^1$H-NMR (400 MHz, DMSO-d6) δ=9.82 (s, 1H), 8.61 (br. s, 1H), 8.02 (d, J=1.6 Hz, 1H), 7.94 (br. s, 1H), 7.75 (d, J=8.0 Hz, 1H), 7.71 (dd, J=1.6, 8.4 Hz, 1H); MS (ESI): [M+H⁺]=378.7.

Step 6: 6-(Trifluoromethoxy)benzo[d][1,3]selenazol-2-amine (IX)

To a stirred solution of 1-(2-bromo-4-((trifluoromethyl)thio)phenyl)selenourea (66) (400.0 mg, 1.06 mmol) in DMSO (6 mL) was added CuI (20.2 mg, 0.11 mmol) and 1,10-phenanathroline (19.1 mg, 0.11 mmol) at 20° C., followed by addition of Cs₂CO₃ (172.4 mg, 0.53 mmol). The reaction was stirred at 80° C. under nitrogen for 20 min. The mixture was quenched with ice-water (60 mL), extracted with EtOAc (2×30 mL). The combined organic phase was washed with saturated brine water solution (50 mL), dried over anhydrous Na₂SO₄ and concentrated. The residue was purified by prep-HPLC to afford the titled compound IX (40 mg, 13%) as a white solid. $^1$H-NMR (400 MHz, DMSO-d6) δ=8.21 (s, 1H), 7.62 (d, J=8.4 Hz, 1H), 7.48 (d, J=9.2 Hz, 1H); MS (ESI): [M+H⁺]=298.8.

Example 10

6-(Pentafluorosulfanyl)-1H-benzo[d]imidazol-2-amine (X)

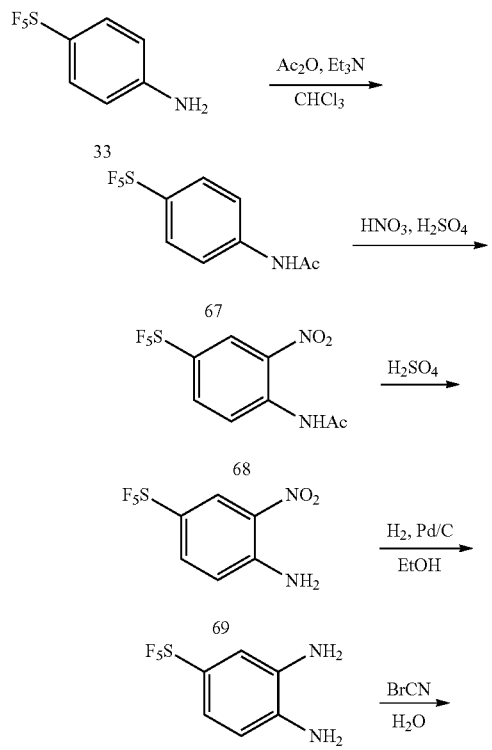

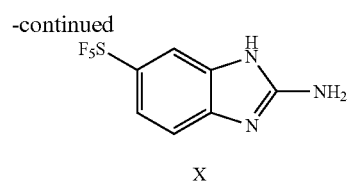

Step 1: N-(4-(pentafluorosulfanyl)phenyl)acetamide (67)

To a stirred solution of 4-(pentafluorosulfanyl)aniline (33) (100 mg, 0.46 mmol) in CHCl₃ (1 mL) was added Et₃N (92.3 mg, 0.92 mmol), followed by addition of Ac₂O (61.2 mg, 0.46 mmol). The reaction was stirred at 20° C. for 3 h, to which H₂O (20 mL) was added. The mixture was extracted with CH₂Cl₂ (2×10 mL). The combined organic phase dried over anhydrous Na₂SO₄ and concentrated to afford the titled crude compound 67 (110 mg, 92%) as a yellow solid, which was used for the next step without further purification. $^1$H-NMR (400 MHz, CDCl₃) δ=7.70 (d, J=9.2 Hz, 2H), 7.62 (d, J=8.8 Hz, 2H), 7.42 (br. s, 1H), 2.22 (s, 3H); MS (ESI): [M+H⁺]=261.8.

Step 2: N-(2-nitro-4-(pentafluorosulfanyl)phenyl)acetamide (68)

To a solution of N-(4-(pentafluorosulfanyl)phenyl)acetamide (67) (110 mg, 0.42 mmol) in conc. H₂SO₄ (1 mL) was added HNO₃ (0.3 mL, 65%) dropwise at ice-bath. The reaction was stirred at 0-20° C. for 1 h. After that, the reaction mixture was poured into ice-water (30 mL), extracted with CH₂Cl₂ (2×15 mL). The combined organic phase dried over anhydrous Na₂SO₄ and concentrated to afford the titled crude compound 68 (120 mg, 93%) as a yellow solid, which was used for the next step without further purification. $^1$H-NMR (400 MHz, CDCl₃) δ=10.49 (br. s, 1H), 8.99 (d, J=9.6 Hz, 1H), 8.65 (d, J=2.4 Hz, 1H), 8.00 (dd, J=2.4, 9.6 Hz, 1H), 2.34 (s, 3H).

Step 3: 2-Nitro-4-(pentafluorosulfanyl)aniline (69)

N-(2-nitro-4-(pentafluorosulfanyl)phenyl)acetamide (68) (120 mg, 0.39 mmol) was dissolved in conc. H₂SO₄ (1 mL), and the reaction was stirred at 100° C. for 15 min. The mixture was cooled to 30° C. and poured into crushed ice, stirred for 10 min and extracted with CH₂Cl₂ (2×15 mL). The combined organic phase was washed with water (20 mL) and brine (20 mL) successively, dried over anhydrous Na₂SO₄ and concentrated. The crude titled compound 69 (100 mg, 97%) was obtained as a yellow solid, which was used for the next step without further purification. $^1$H-NMR (400 MHz, CDCl₃) δ=8.58 (d, J=2.4 Hz, 1H), 7.70 (dd, J=2.4, 9.2 Hz, 1H), 6.85 (d, J=9.6 Hz, 1H), 6.40 (br. s, 2H).

Step 4: 4-(Pentafluorosulfanyl)benzene-1,2-diamine (70)

To a solution of 2-nitro-4-(pentafluorosulfanyl)aniline (69) (100 mg, 0.39 mmol) in EtOH (2 mL) was added Pd/C (100 mg, 10%). The reaction was stirred at 20° C. under H₂ atmosphere for 16 h. The reaction mixture was filtered, and the filtrate was concentrated to afford the crude titled compound 70 (70 mg, 80%) as a yellow solid. MS (ESI): [M+H⁺]=234.8.

Step 5: 6-(Pentafluorosulfanyl)-1H-benzo[d]imidazol-2-amine (X)

To a stirred solution of 4-(pentafluorosulfanyl)benzene-1,2-diamine (70) (70 mg, 0.30 mmol) in $H_2O$ (1 mL) was added BrCN (32.3 mg, 0.31 mmol). The reaction was stirred at 100° C. under nitrogen for 8 h. The reaction mixture was diluted with $H_2O$ (20 mL), treated with $NH_4OH$ (25%) until pH 10-11, and then extracted with EtOAc (2×10 mL). The combined organic phase was washed with saturated brine water solution (20 mL), dried over anhydrous $Na_2SO_4$ and concentrated. The residue was purified by prep-TLC (silica gel, $CH_2Cl_2$/MeOH=8:1) to afford the titled compound X (30 mg, 38%) as a light-yellow solid. $^1$H-NMR (400 MHz, DMSO-d6) δ=11.14 (br. s, 1H), 7.55 (s, 1H), 7.37 (d, J'$^2$ 7.2 Hz, 1H), 7.19 (d, J=8.4 Hz, 1H), 6.71 (br. s, 2H); MS (ESI): $[M+H^+]$=259.8.

Example 11

Pharmacological Studies

In the example, the pharmacological property is described in detail with the compound having formula I-XXII.

A. Inhibitory Effect of Compound I-XXII on Human Voltage-Gated Sodium Channels

Figure 1A:
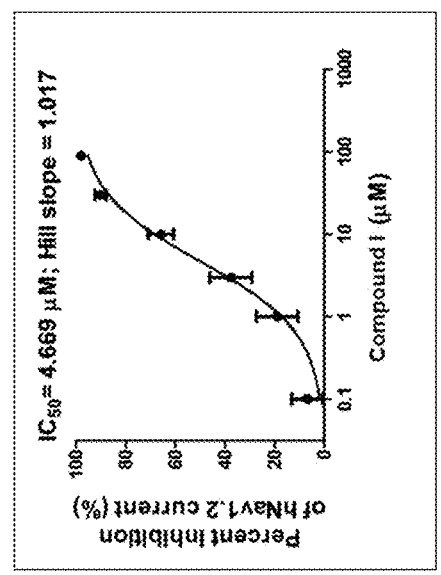

The potential inhibitory effect of Compound I-XXII on human voltage-gated sodium channels (hNav1.2/1.7) was evaluated by manual patch-clamp system according to the procedures as described. HEK293 cell line stably transfected with SCN2A/SCN9A gene was employed in this study and Tetrodotoxin (TTX) was used as a positive control to ensure the good quality of the assay. The results are shown in the following Table 1, while the fitting dose-response curves for Compound I are shown in FIGS. 1A and 1B.

General procedure: HEK 293 cells were stably transfected with human Nav1.2 or Nav1.7 voltage-gated sodium channels. The cells are routinely maintained in culture medium containing in 90% DMEM, 10% FBS, 100 U/mL Penicillin-Streptomycin and 400 mg/ml of G418. Before the assay, the cells were resuspended and plated onto the coverslips at 5×105 cells/per 6 cm cell culture dish for use. The voltage-gated Nav1.2 and Nav1.7 channel current was recorded at room temperature (25° C.) from randomly selected transfected cells under whole-cell patch clamp systems equipped with EPC 10 USB (HEKA) or Multiclamp 700B amplifier (Molecular Devices), while electrical data was digitalized by Digidata1440A with sampling frequency over 10 kHz and acquired with Patchmaster or pClamp10 respectively. The glass electrode with resistance ranged from 2 to 3.5 MW was prepared by micropipette puller P-97 (Sutter Instrument) and filled with internal solutions (in mM): 140 KCl, 2 $MgCl_2$, 10 EGTA, 10 HEPES and 5 MgATP (pH adjusted to 7.35 with KOH), while cells were bathed in extracellular solutions (in mM) 132 NaCl, 4 KCl, 3 $CaCl_2$, 0.5 $MgCl_2$, 11.1 glucose, and 10 HEPES (pH adjusted to 7.35 with NaOH). After rupture, the series membrane resistance was at least 50% compensated and capacitance was also compensated as well. All cells were voltage-clamped to a holding potential of −80 mV unless otherwise specified. The inward sodium currents were elicited by a 20-ms voltage pulse to 10 mV from −80 mV applied every 15 s. The sodium current was initially recorded for at least 120 seconds to assess the current stability, and only cells with recording parameters over acceptance criteria was finally used to assess the dose response to the local perfusion of Compound I-XXII. The blank vehicle was firstly applied to the patched cells in order to establish the recording baseline. After at least 5 min when the elicited sodium currents reaches stabilization, the test compound was perfused into recording chamber accumulatively from low to high concentrations. The positive control article, Tetrodotoxin (TTX), was also used to challenge same batch of cell in order to ensure the good performance of the recording system. All experiments were performed in triplicate for $IC_{50}$ determination. Upon data acquisition, the PatchMaster or pClamfit software were used to extract the peak current from the original raw data, while the peak current inhibition was defined by equation as shown below.

$$\text{Peak current inhibition} = \left(1 - \frac{\text{Peak current}_{compound}}{\text{Peak current}_{vehicle}}\right) \times 100$$

The dose response curve for the test compound was plotted with % inhibition against the dose concentration of the test compound using Graphpad Prism 5.0 software, and then the data was fit to a sigmoid dose-response curve with variable slope for $IC_{50}$ determination.

TABLE 1

Inhibitory effect of the test compound on human Nav1.2/1.7 channels

| Test Article | hNav1.2 $IC_{50}$ (μM) | hNav1.7 $IC_{50}$ (μM) |
| --- | --- | --- |
| Compound I | 4.669 | 0.682 |
| Compound V | 4.372 | 0.722 |
| Compound VI | 10.144 | 0.745 |
| Compound VII | 18.038 | 1.365 |
| Compound IX | 15.312 | 1.174 |

B. Compound I Testing on Mechanical Allodynia in SNL (Spinal Nerve Ligation) Rats SNL model is a commonly used model to measure surgical induced neuropathic pain. The goal of the study was to evaluate the efficacy of Compound I to attenuate mechanical allodynia in SNL model in Sprague-Dawley rats.

In this study, SNL model was created following typical procedure and the approved drug Tapentadol (XW-TAP) was used as reference compound. Gabapentin was applied as positive control for model validation.

Experimental groups are showed in Table 2.

TABLE 2

Experimental groups.

| Group | Model | Treatment | Dose (mg/kg) | Dose Volume (mL/kg) | Route of Admin | Test time point | N |
| --- | --- | --- | --- | --- | --- | --- | --- |
| 1 | SNL | Compound I | 5 | 5 | i.p. | 0.5 h | 10 |
| 2 | SNL | Tapentadol | 10 | 5 | i.p. | 0.5 h | 10 |

Dose Formulation:

1) 5 mg/kg Compound I: Added 17.13 mg Compound I to 16.96 mL 0.5% methylcellulose in normal saline solution, vortexed to fully mix.

2) 10 mg/kg Tapentadol: Added 39.39 mg Tapentadol to 16.81 mL normal saline solution, vortexed to fully mix.

Procedures for Mechanical Allodynia Measurement:

1) Rats were placed individually in a plastic enclosure with a mesh bottom which allowed full access to the paws. Rats were acclimated for 15 min prior to testing.

2) After acclimation, the mid-plantar hind paw was touched with one of a series of eight von Frey hairs with logarithmically incremental stiffness as follows: 3.61 (0.4 g), 3.84 (0.6 g), 4.08 (1 g), 4.31 (2 g), 4.56 (4 g), 4.74 (6 g), 4.93 (8 g) and 5.18 (15 g). The von Frey hairs were presented perpendicularly to the plantar surface with sufficient force to cause slight buckling against the paw and held for approximately 6-8 s. Stimulation was presented at intervals of 5 seconds, allowing for apparent resolution of any behavioral responses to previous stimulus. A positive response was noted if the paw was sharply withdrawn. Flinching immediately upon removal of the hair was also considered as a positive response. Ambulation was considered as an ambiguous response and in such cases, the stimulus was repeated.

3) Starting with filament 4.31 (2 g), depending on response or no response, investigator used a filament of decreasing or increasing force, respectively based on Dixon up-down method. Positive responses included an obvious withdrawal of the hind paw from the filament, or flinching behavior immediately following removal of the filament. The maximum force applied was filament 5.18 (15 g).

Habituation and pre-dose mechanical allodynic baseline measurement:

Ten days after surgery, the rats were habituated in the testing environment for 15 min before allodynia measurement for three days. Pre-dose baseline was taken on day 13. Rats that didn't show allodynic response at this point were excluded (Rats with a paw withdrawal threshold >5 g).

Figure 2:
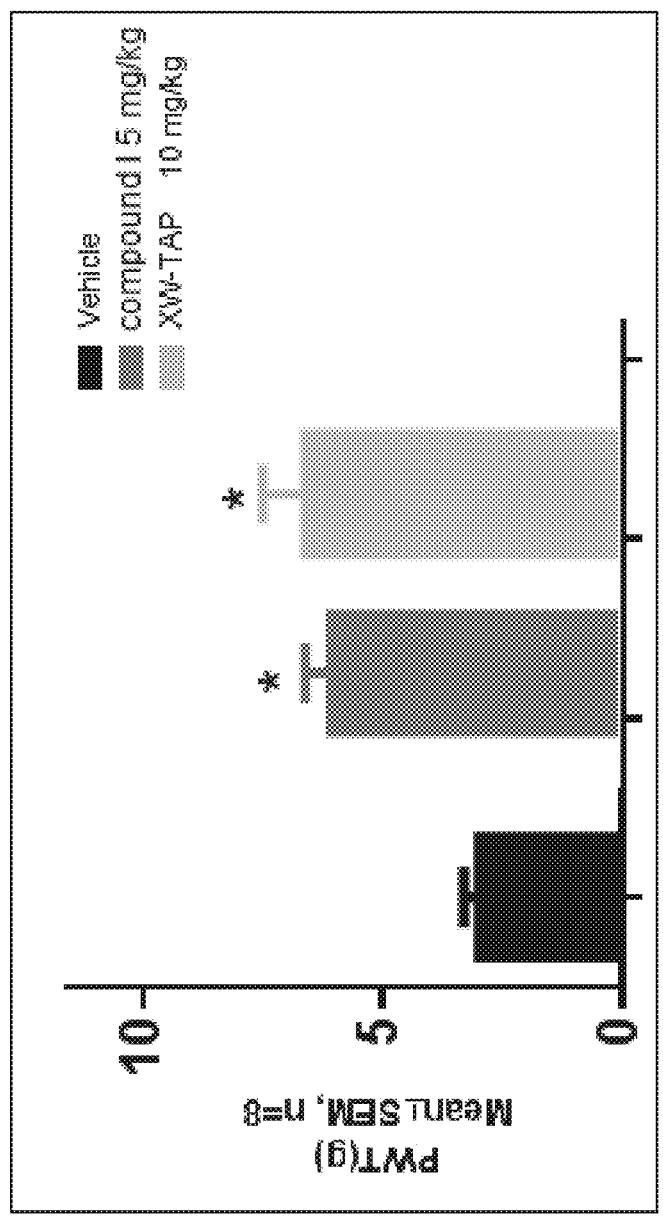
FIG. 2 shows the anti-allodynic effects of the Compound I in SNL rats.

FIG. 2 shows the anti-allodynic effects of the compounds in SNL rats. (*p<0.05 vs). Vehicle group by one-way ANOVA followed by Dunnett's Multiple Comparison Test.

Results shows that Compound I reversed SNL-induced mechanical allodynia at the dose of 5 mg/kg at 0.5 h time point post dose.

C. Pharmacokinetic Studies

For rat pharmacokinetic studies, male Sprague-Dawley rats were housed individually and fasted overnight before use. The animal dosing experiments were carried out in accordance to the National Institutes of Health Guide to the Care and Use of Laboratory Animals and the Animal Welfare Act. For Compound I, a single dose of 5.8 mg/kg was administered to each rat in two groups (n=5/group) via intravenous (IV) and oral (PO) administration, respectively. The vehicle used for IV administration was 10% (v/v) CremophorEL in 90% PBS. The vehicle used for PO administration was 0.5% (w/v) methylcellulose in normal saline solution. Blood samples were collected at specified timepoints (pre-dose, 30 minutes, 1 hour, 2 hours, 4 hours, 7 hours, 8 hours, 12 hours, 24 hours) following administration to individual rats within IV and PO group. Blood samples were clotted on ice immediately, plasma samples were then isolated by centrifugation and stored frozen (−80° C.) until further analysis. The concentrations of Compound I were individually determined by LC/MS/MS assay. Various pharmacokinetic parameters were calculated using Phoenix™ WinNonlin® software. To quantify the bioconversion efficiency of the Compound I in the circulation system, the bioavailability of Compound I after PO administration was calculated.

Figure 3:
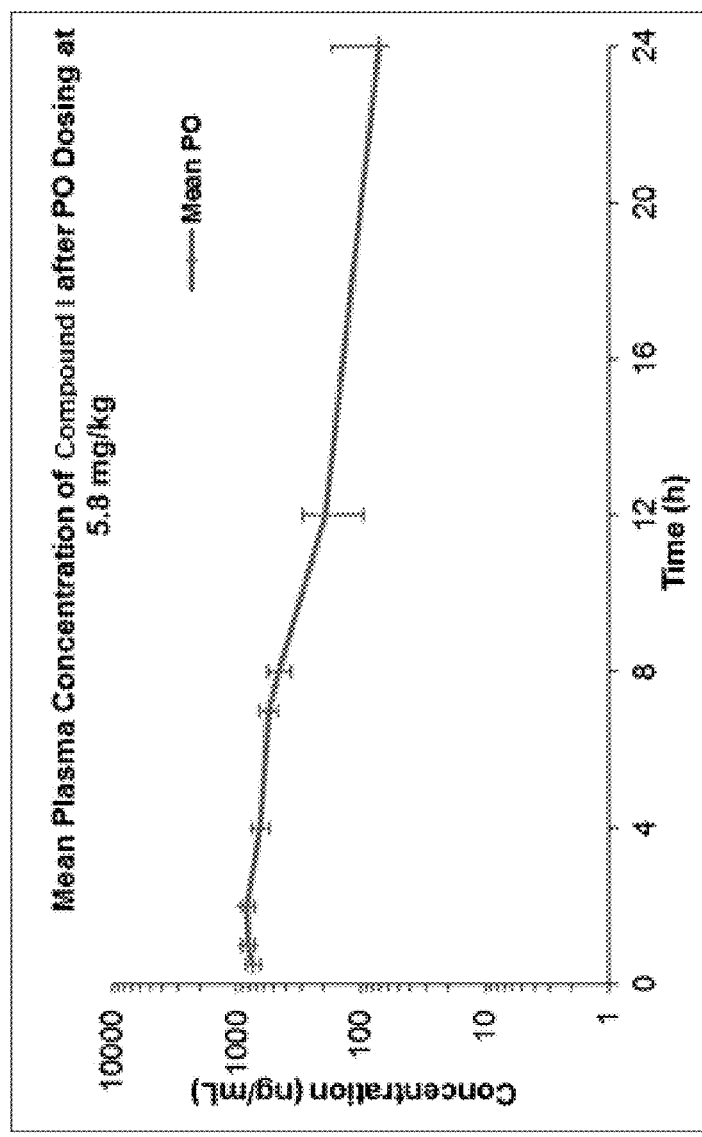
FIG. 3 shows the pharmacokinetic parameters of Compound I in rats.

The results are showed in Table 3 and FIG. 3.

TABLE 3

Rat pharmacokinetic parameters of Compound I.

| | | $AUC_{0\text{-}last}$ (h * ng/mL) | $T_{1/2}$ (h) | $T_{max}$ (h) | $C_{max}$ (ng/mL) |
|---|---|---|---|---|---|
| Compound I at 5.8 mg/kg | PO | 7692 | 7.11 | 2.30 | 942 |

Finally, it should be noted that there are other ways to practice the invention. Accordingly, embodiments of the present invention is to be described as examples, but the present invention is not limited to the contents described, further modifications may be made within the scope of the present invention or the equivalents added in the claims.

All publications or patents cited herein are incorporated by reference in this invention.

Reference throughout this specification to "an embodiment", "some embodiments", "one embodiment", "another example", "an example", "a specific examples" or "some examples" means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. The compound 6-(pentafluoro-$\lambda^6$-sulfaneyl)benzo[d]thiazol-2-amine (I):

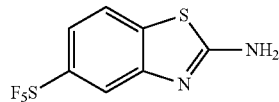

or a pharmaceutically acceptable salt thereof.

2. The compound 6-(pentafluoro-$\lambda^6$-sulfaneyl)benzo[d][1,3]selenazol-2-amine (V):

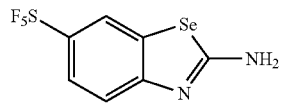

or a pharmaceutically acceptable salt thereof.

3. The compound 6-(trifluoromethyl)benzo[d][1,3]selenazol-2-amine (VI):

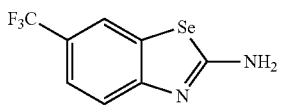

or a pharmaceutically acceptable salt thereof.

4. The compound 6-((trifluoromethyl)thio)benzo[d][1,3]selenazol-2-amine (IX):

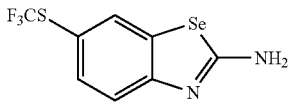

or a pharmaceutically acceptable salt thereof.

5. A pharmaceutical composition comprising:
a therapeutically effective amount of the compound of claim 1 or a pharmaceutically acceptable salt thereof; and
a pharmaceutically acceptable excipient, carrier, adjuvant, solvent, or a combination of any of the foregoing.

6. The pharmaceutical composition of claim 5, wherein the pharmaceutical composition is a transdermal formulation.

7. The pharmaceutical composition of claim 5, wherein the pharmaceutical composition is an oral formulation.

8. A pharmaceutical composition comprising:
a therapeutically effective amount of the compound of claim 2 or a pharmaceutically acceptable salt thereof; and
a pharmaceutically acceptable excipient, carrier, adjuvant, solvent, or a combination of any of the foregoing.

9. The pharmaceutical composition of claim 8, wherein the pharmaceutical composition is a transdermal formulation.

10. The pharmaceutical composition of claim 8, wherein the pharmaceutical composition is an oral formulation.

11. A pharmaceutical composition comprising:
a therapeutically effective amount of the compound of claim 3 or a pharmaceutically acceptable salt thereof; and
a pharmaceutically acceptable excipient, carrier, adjuvant, solvent, or a combination of any of the foregoing.

12. The pharmaceutical composition of claim 11, wherein the pharmaceutical composition is a transdermal formulation.

13. The pharmaceutical composition of claim 11, wherein the pharmaceutical composition is an oral formulation.

14. A pharmaceutical composition comprising:
a therapeutically effective amount of the compound of claim 4 or a pharmaceutically acceptable salt thereof; and
a pharmaceutically acceptable excipient, carrier, adjuvant, solvent, or a combination of any of the foregoing.

15. The pharmaceutical composition of claim 14, wherein the pharmaceutical composition is a transdermal formulation.

16. The pharmaceutical composition of claim 14, wherein the pharmaceutical composition is an oral formulation.

* * * * *

UNITED STATES PATENT AND TRADEMARK OFFICE
CERTIFICATE OF CORRECTION

PATENT NO. : 10,640,476 B2  
APPLICATION NO. : 16/587571  
DATED : May 5, 2020  
INVENTOR(S) : Jia-Ning Xiang, Xuesong Xu and Wei Zhou Page 1 of 1

It is certified that error appears in the above-identified patent and that said Letters Patent is hereby corrected as shown below:

In the Claims

Column 74, Claim 1, Line 50 that reads " 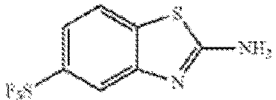 " should read

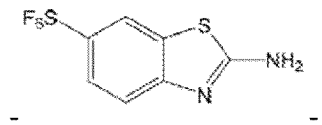

Signed and Sealed this  
Seventh Day of September, 2021

Drew Hirshfeld  
*Performing the Functions and Duties of the*  
*Under Secretary of Commerce for Intellectual Property and*  
*Director of the United States Patent and Trademark Office*